US011298398B2

(12) United States Patent
Huang

(10) Patent No.: US 11,298,398 B2
(45) Date of Patent: Apr. 12, 2022

(54) METHOD OF TREATING A PHILADELPHIA CHROMOSOME-POSITIVE TUMOR

(71) Applicant: Mallen Huang, Uppsala (SE)

(72) Inventor: Mallen Huang, Uppsala (SE)

( * ) Notice: Subject to any disclaimer, the term of this patent is extended or adjusted under 35 U.S.C. 154(b) by 63 days.

(21) Appl. No.: 16/985,393

(22) Filed: Aug. 5, 2020

(65) Prior Publication Data
US 2021/0077565 A1 Mar. 18, 2021

Related U.S. Application Data

(63) Continuation of application No. 10/551,804, filed as application No. PCT/SE2004/000589 on Apr. 14, 2004, now Pat. No. 10,799,553.

(30) Foreign Application Priority Data

Apr. 14, 2003 (SE) .................................. 0301109-5

(51) Int. Cl.
A61K 38/08 (2019.01)
A61K 39/00 (2006.01)
(52) U.S. Cl.
CPC .......... *A61K 38/08* (2013.01); *A61K 39/0011* (2013.01); *A61K 2039/5154* (2013.01); *A61K 2039/5156* (2013.01); *A61K 2039/53* (2013.01)
(58) Field of Classification Search
None
See application file for complete search history.

(56) References Cited

U.S. PATENT DOCUMENTS

| 7,385,023 | B1 | 6/2008 | Schultze et al. |
| 10,799,553 | B2 * | 10/2020 | Huang .................... A61P 31/04 |
| 2003/0181406 | A1 | 9/2003 | Schetter et al. |
| 2003/0202963 | A1 | 10/2003 | Crystal et al. |
| 2004/0146492 | A1 | 7/2004 | Hwu et al. |
| 2004/0186067 | A1 | 9/2004 | Krieg et al. |
| 2004/0198680 | A1 | 10/2004 | Krieg |

FOREIGN PATENT DOCUMENTS

| JP | 2006-508023 A | 3/2006 |
| WO | 96/00255 A1 | 1/1996 |
| WO | 00/15264 A1 | 3/2000 |
| WO | 00/54839 A2 | 9/2000 |
| WO | 01/11067 A1 | 2/2001 |
| WO | 01/83785 A2 | 11/2001 |
| WO | 02/069900 A2 | 9/2002 |
| WO | 2004/073641 A2 | 9/2004 |

OTHER PUBLICATIONS

Kaisho, Tsuneyasu et al., Toll-like receptors as adjuvant receptors, Biochimica et Biophysica Acta, vol. 1589, pp. 1-13 (2002).
Nl, Houping et al., Extracelluar mRNA Induces Dendritic Cell Activation by Stimulating Tumor Necrosis Factor-a Secretion and Signaling through a Nucleotide Receptor, The Journal of Biological Chemistry, vol. 277, No. 15, pp. 12689-12696 (Apr. 12, 2002).
Jin, Zhaoyu et al., Overview of Cell Death Signaling Pathways, Cancer Biology & Therapy, vol. 4, No. 2, pp. e50-e74 (Feb. 2005).
Krug Anne et al., Toll-like receptor expression reveals CpG DNA as a unique micorbial stimulus for plasmacytoid dendritic cells which synergizes with CD40 ligand to induce high amounts of IL-12, Eur. J. Immunol, vol. 31, pp. 3026-3037 (2001).
Kikuchi, Toshiaki et al., Dendritic cells modified to express CD40 ligand elicit therapeutic immunity against preexisting murine tumors, Blood, vol. 96, No. 1, pp. 91-99 (Jul. 1, 2000).
Kontani, Keiichi et al., Novel vaccination protocol consisting of injecting MUC1 DNA and nonprimed dendritic cells at the same region greatly enhanced MUC1-specific antitumor immunity, Cancer Gene Therapy, vol. 9, pp. 330-337 (2002).
Wang, Ruobing et al., Induction of Antigen-Specific Cytotoxic T Lymphocytes in Humans by a Malaria DNA Vaccine, Science, vol. 282, pp. 476-480 (Oct. 16, 1998).
Donnelly, John J. et al., DNA Vaccines, Annu. Rev. Immunol, vol. 15, pp. 617-648 (1997).
Gurunathan, Sanjay et al., DNA Vaccines: Immunology, Application, and Optimization, Annu. Rev. Immunol, vol. 18, pp. 927-974 (2000).
Timmerman, MD, John M. et al., Dentritic Cell Vaccines for Cancer Immunotherapy, Annu. Rev. Med., vol. 50, pp. 507-529 (1999).
Hsu, Ching-Hsiang et al., Immunoprophylaxis of allergen-induced immunoglobulin E synthesis and airway hyperresponsiveness in vivo by genetic immunization, Nature Medicine, vol. 2, No. 5 (May 1996).
Waisman, Ari et al., Suppressive vaccination with DNA encoding a variable region gene of the T-cell receptor prevents autoimmune encephalomyelitis and activates Th2 immunity, Nature Medicine, vol. 2, No. 8, pp. 899-905 (Aug. 1996).
Fonteneau, Jean-Francois et al., Activation of infuenza virus specific CD4+ and CD8+ T cells: a new role for plasmacytoid dendritic cells in adaptive immunity, Blood First Edition Paper, prepublished First Edition Paper for Blood, vol. 101, No. 9, pp. 3520-3526 (2003).
Brenner Malcolm et al., Tranfusion Medicine: New Clinical Applications of Cellular Immunotherapy, American Society of Hmatology, pp. 356-375 (2000).
Hornung, Veit et al., Quantitative Expression of Toll-Like Receptor 1-10 mRNA in Cellular Subsets of Hunam Peripheral Blood Mononuclear Cells and Sensitivity to CpG Oligodeoxynucleotides1, The American Association of Immunologists, vol. 168, pp. 4531-4537 (2002).
Spitler, M.D., Lynn E., Cancer Vaccines: The Interferon Analogy, Cancer Biotherapy, vol. 10, No. 1, pp. 1-3 (1995).
Boon, Thierry et al., Human T Cell Responses Against Melanoma, Annu. Rev. Immunol, vol. 24, pp. 175-208 (2006).

(Continued)

*Primary Examiner* — Phillip Gambel

(74) *Attorney, Agent, or Firm* — Porter Wright Morris & Arthur LLP

(57) ABSTRACT

A method of treating a Philadelphia chromosome-positive tumor in a subject comprises administering to the subject a therapeutic composition comprising an incubated combined mixture of (a) a first component comprising (i) Philadelphia chromosome-positive tumor lysate, (ii) plasmid encoding bcr/abl fusion protein, or (iii) bcr/abl fusion peptide; and (b) a second component comprising plasmacytoid dendritic cells expressing Toll-like receptor 9 and modified for stable expression of CD40 ligand or GM-CSF by a nucleotide sequence engineered into said plasmacytoid dendritic cells.

9 Claims, 21 Drawing Sheets

Specification includes a Sequence Listing.

(56) References Cited

OTHER PUBLICATIONS

Slingluff Jr., M.D., Craig L., The Present and Future of Peptide Vaccines for Cancer: Single or Multiple, Long or Short, Alone or in Combination?, Cancer J., vol. 17, No. 5, pp. 343-350 (Sep. 2011).
Nl, Humping et al., Detection of bcr/abl fusion transcripts by semiquantitative multiplex RT-PCR combined with a colormetric assay in Ph positive leukemia, Cancer Letters, vol. 124, pp. 173-180 (1998).
Tanaka, Yuji et al., Generation of HLA-DRB1*1501-restricted p190 minor bcr-abl (e1a2)-specific CD4+ T lymphocytes, British Journal of Hemotology, vol. 109, pp. 435-437 (2000).
Pullarkart, et. al., Lymphoid Dendritic Cells Mobilized with Progeniporitin Induce Th1 and Peptide-specific Cytetoxic T Cell Responses, Blood, vol. 98, No. 11, Part 1, pp. 297a (2001).

\* cited by examiner

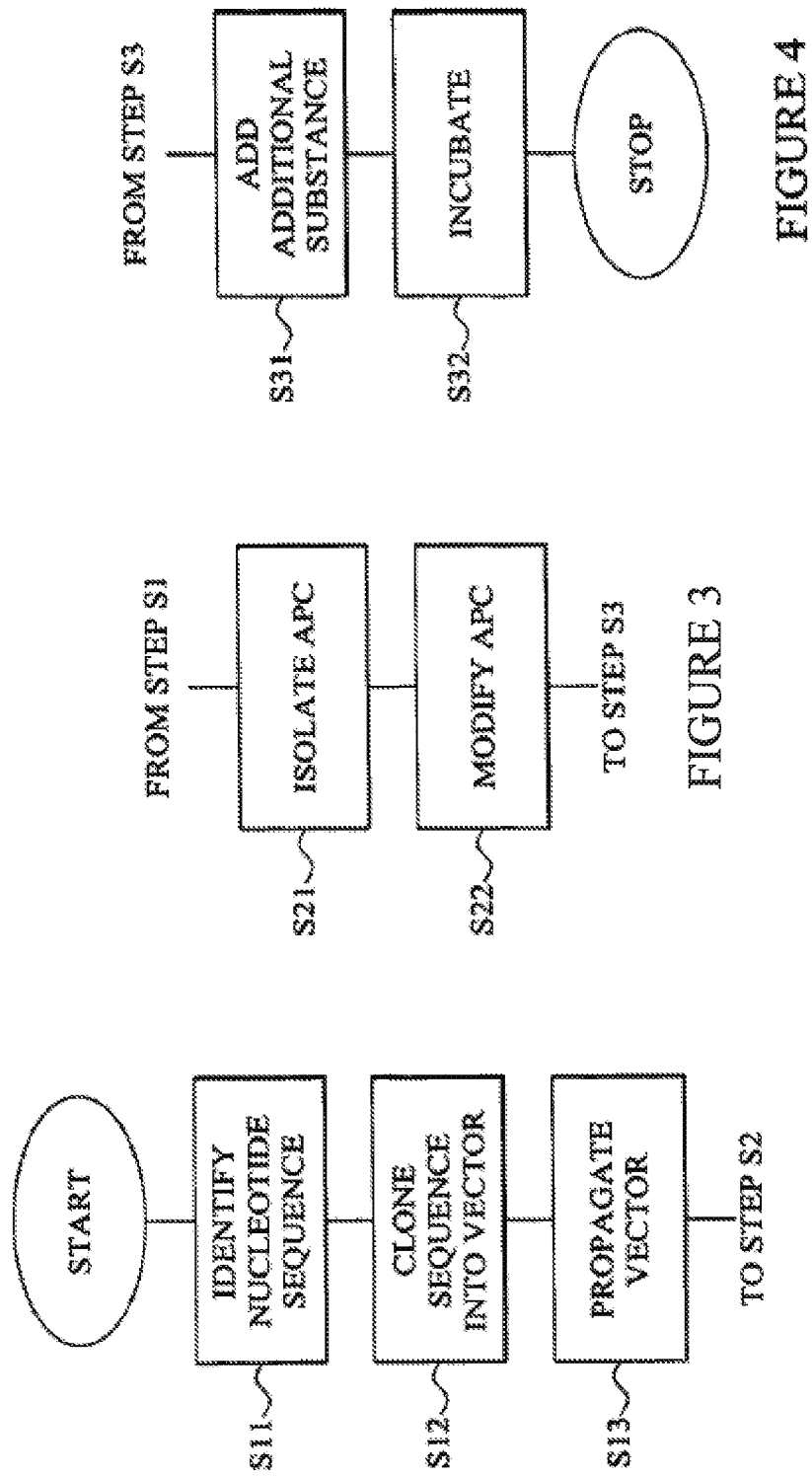

Moloney murine leukemia virus

Retrovirus vector containing mCD40L gene

A tumor-bearing mouse model for therapeutic and protective vaccinations

METHOD OF TREATING A PHILADELPHIA CHROMOSOME-POSITIVE TUMOR

The sequence listing submitted herewith, entitled "Aug. 5, 2020-Sequence-Listing_ST25.txt", created Aug. 5, 2020 and having a size of 3636 bytes, is incorporated herein by reference.

TECHNICAL FIELD

The present invention generally refers to vaccine compositions and in particular to a vaccine composition containing of nucleotide sequences and gene-modified antigen presenting cells and use thereof.

BACKGROUND OF THE INVENTION

Vaccination approaches utilizing nucleotide sequences, including DNA or RNA sequences, have been developed during the last decade. DNA vaccines are easy to construct, stable and cost effective to produce. In addition, DNA vaccines can be repeatedly administrated without significant generation of vector-specific immune response. When naked plasmid DNA is injected into the skin and muscle of mice, the DNA is taken up by neighboring cells. These nonlymphoid tissues express the plasmid-encoded protein and the antigenic peptide is then presented to T cells in the context of the major histocompatibility complex (MHC) class I or class II molecules. (*Annu. Rev. Immunel.* 2000, 18:927).

DNA immunization has been studied in animal models against various infectious pathogens and malignancies (*Annu Rev. Immunol.* 1997, 15:617-648). DNA vaccination has been shown to suppress autoimmune diseases and to inhibit allergic responses (*Nat. Med.* 1996 2:899-905, *Nat. Med.* 1996, 2:540-544). Recent studies of DNA vaccines demonstrated the generation of a cellular immune response against malaria infection and HIV peptides in humans (*Science* 1998, 282:476-480, *Lancet* 1998, 351:1320-1325).

Typically, plasmid DNA vector has two major units: (1) a plasmid backbone that delivers adjuvant and (2) a transcriptional unit comprising a promoter, antigen nucleotide sequence and poly-adenylation addition sequence, which together direct protein synthesis.

The major problem for the existing DNA vaccines today is that they are not as effective as expected. Disappointing results from ongoing preclinical work and from clinical trials have put a serious doubt about the utility of DNA vaccines. Therefore, improvement of vaccine efficiency has become a critical goal in the development of DNA vaccinations.

Dendritic cells (DCs) are professional antigen-presenting cells (APCs) of hemopoietic origin. DCs represent cell types of multiple lineages with various functions, although all DCs share features related to their common antigen (Ag) processing and T cell activation machinery.

Tumors express a number of protein antigens that can be recognized by T cells providing potential targets for cancer immunotherapy intervention. Dendritic cells (DCs) are uniquely potent in their ability to present antigens to T cells. This property has been used to develop therapeutic cancer vaccines. In clinical trials of DC vaccination against non-Hodgkin's lymphoma and melanoma, induction of anti-tumor immune responses and tumor regressions has been observed (*Annu Rev Med.* 1999, 50:507-529).

SUMMARY OF THE INVENTION

It is a general object of the present invention to provide a novel vaccine composition.

It is an object of the invention to provide a method to produce the vaccine composition.

It is another object of the invention to provide a pharmaceutical composition.

It is a further object of the invention to provide a vaccine composition comprising a nucleotide sequence encoding antigenic molecule and modified antigen-presenting cells, preferably without limitation, dendritic cells.

It is a particular object of the invention to provide a vaccine composition usable for preventing and/or treating cancer, infectious diseases, Alzheimer, allergy, autoimmune diseases or blood disorders.

It is another particular object of the invention to provide a vaccine composition comprising of a subtype of dendritic cells, namely plasmacytoid dendritic cells (pDCs)/interferon-producing cells (IPCs), which are genetically engineered to express immune-modulating molecules.

These and other objects are met by the invention as defined by the accompanying patent claims.

Briefly, the present invention provides a novel vaccine composition comprising a nucleotide sequence encoding an antigenic molecule and gene-modified antigen-presenting cells (APCs), preferably provided as a pre-incubated mixture of the nucleotide sequence and the gene-modified APCs. The nucleotide sequence that encodes antigen could be a naked DNA or RNA sequence. In addition, the nucleotide sequence encoding antigen is preferably inserted and included in a vector, where the nucleotide sequence is provided under transcriptional control of a promoter, enhancer and/or other regulatory sequences. The vector of the invention is preferably a plasmid DNA vector containing the gene that encodes the antigen. The vector may preferably also comprise other nucleotide sequences, which can modulate or regulate the host immune response of a subject, preferably mammalian subject and more preferably human subject, receiving the vaccine composition. Such an immune response modulating sequence could be the unmethylated cytidine-phosphate-guanosine (CpG) motifs, or a gene sequence coding for xenogenic molecules (proteins/peptides) participating in modulating the immune response of the subject.

The APCs used in the present vaccine composition are cell types adapted for processing and presenting antigens to other cells, especially to CD4+ and CD8+ T cells of the immune system. Examples of preferred APCs include professional APCs, such as DCs, IPCs, macrophages, monocytes and B cells. A particular preferred cell type of APCs is cells having pDC/IPCs characteristics and functions, in particular by expressing Toll-like receptor 9 (TLR9) and P2X7 receptor, secreting cytokines and producing large amount of type I IFN-α and IFN-β upon microbial stimulation, and stimulating effector cells in the immune system.

Furthermore, the APCs are genetically modified, or otherwise engineered, to express immune response modulating molecules. Such molecules could enhance the immune response of a subject by increasing antigen presentation, stimulating secretion of Th1 or Th2 cytokines, activating the APCs, Langerhans cells and effector cells and/or enhancing the immune response. Alternatively, especially for autoimmune diseases and allergy, the immune response modulating molecules could help to suppress the immune response or induces immune tolerance or anergy in a subject. Suitable genes used for modifying APCs include, for example, cytokine genes, interleukins, adhesion molecules, interferon genes, chemokine genes and chemokine receptor genes and genes coding for heat shock proteins, tumor necrosis factors (TNF), anti-apoptosis agents, apoptosis-inducing molecule, growth factors and pharmaceutically accepted carriers.

The vaccination composition of the invention may contain additional molecules besides the nucleotide sequence and APCs. Such additional molecules may enhance or suppress the immune response of a subject, increase antigen presentation of APCs, stimulating secretion of Th1 or Th2 cytokines, activating the APCs, Langerhans cells, effector cells and/or regulating the immune functionality of APCs.

The presently most preferred vaccine composition of the invention includes gene-modified pDCs or type I IFN producing cells (IPCs) and plasmid DNA encoding MHC-binding antigen and having CpG-motifs.

The present invention also refers to a method of treating and/or preventing a disorder or disease by administering the vaccine composition of the invention to a subject, preferably mammalian subject and more preferably human subject, in need thereof. The present invention preferably includes nucleotide sequences encoding disease-associated antigenic molecules. For example, in infectious disease, the nucleotide sequence preferably encodes a protein or peptide originating from the infectious microorganism involved in the disease, such as a viral, bacterial, fungi, protozoa or parasitic peptide or protein. Injection of the nucleotide sequence encoding the protein/peptide of the infectious microorganism together with modified APCs into a subject, preferably human subject and animal subject will evoke a specific immune response against the encoding antigenic protein/peptide.

Cancers are diseases with altered or abnormal gene expression. Proteins in cancer cells expressed in abnormal levels can be used as target for T cell recognition. Nucleotide sequences encoding tumor-associated antigens are preferably included in the vaccine composition of present invention.

The present invention also refers to a method to produce the vaccine composition of present invention. This method comprises identifying MHC-binding antigenic molecule associated with a disease or disorder to be treated or prevented by the vaccine composition. In a preferred embodiment, the nucleotide sequence encoding this identified antigenic molecule is inserted into a plasmid DNA vector, preferably a plasmid vector including unmethylated CpG-motifs. APCs are isolated, preferably from autologous APCs from the subject (or recipient). The APCs are preferably a unique type of dendritic cells, resembling pDCs type and (natural) interferon producing cell type (NIPCs) and has the capacity to produce type I interferon when stimulated by e.g. plasmid DNA. The APCs are then genetically engineered by one or several genes encoding immune co-stimulatory molecules that regulating APCs function and stimulate immune effector cells. Finally, the nucleotide sequence encoding the antigen and the gene-engineered APCs are mixed and incubated completing the method and ending in a preferred embodiment of a vaccine composition of the invention.

Thus, a key feature according to the invention for obtaining the positive results is the usage of gene-modified APCs together with the nucleotide sequence encoding the antigenic molecule. An additional preferred feature of the invention is the pre-incubation of the two main constitutes of the vaccine composition prior to administration.

This pre-incubation allows APCs to endocytose the nucleotide sequence, after internalized into the APCs, the antigenic sequences are processed and presented by APC, whereas, the CpG-motifs bind to different receptors, including TLR9, resulting in activation of the APCs and production of immune modulating molecules, such as type I IFNs and cytokines.

The invention offers the following advantages:
Superior anti-tumor efficiency in tumor-bearing mice compared to prior art DNA vaccine compositions;
Treatment of cancer with the vaccine composition of the invention is 5-fold more effective than using vaccine consisting of nucleotide sequences or plasmid vectors encoding antigen alone;
Priming tumor specific cytotoxic T lymphocytes (CTLs) in vivo is 8-fold more effective for the vaccine composition of the invention than using either plasmid DNA containing nucleotide sequences encoding antigens or tumor-peptide or empty plasmid vectors as vaccines respectively;
Priming tumor specific CTLs in vivo is 2-fold more effective for the vaccine composition of the invention than when using vaccines including only gene-modified APCs loaded with MHC-class I-binding antigenic peptides;
Immunization with the vaccine composition of present invention primes and induces tumor-specific CTLs recognizing tumor peptide presented in the vaccine composition;
The tumor-peptide specific CTLs are 8-fold more frequent induced in tumor-bearing mice treated by the vaccine of invention compared to mice treated with plasmid DNA encoding tumor-peptide;
Eliminates the risk of introducing not fully inactivated pathogens as compared with vaccine compositions based on attenuated or inactivated pathogens;
Vaccine could comprise xenogenic nucleotide sequences for breaking the tolerance of self-antigen and induce immune response against the self-antigen in a subject;
Usable for treating and/or preventing a wide range of diseases and disorders by simply exchanging the nucleotide sequences encoding the antigen; and
Allows introduction of immune-modulating molecules by genetically engineering the antigen-presenting cells of the vaccine composition.

Other advantages offered by the present invention will be appreciated upon reading of the below description of the embodiments of the invention.

SHORT DESCRIPTION OF THE DRAWINGS

The invention together with further objects and advantages thereof, may best be understood by making reference to the following description taken together with the accompanying drawings, in which:

FIG. 2 is a flow diagram illustrating the nucleotide-providing step of the vaccine producing method of FIG. 1;

FIG. 3 is a flow diagram illustrating the APC-providing step of the vaccine producing method of FIG. 1;

FIG. 4 is a flow diagram of additional steps of the vaccine producing method of FIG. 1;

Figure 6:
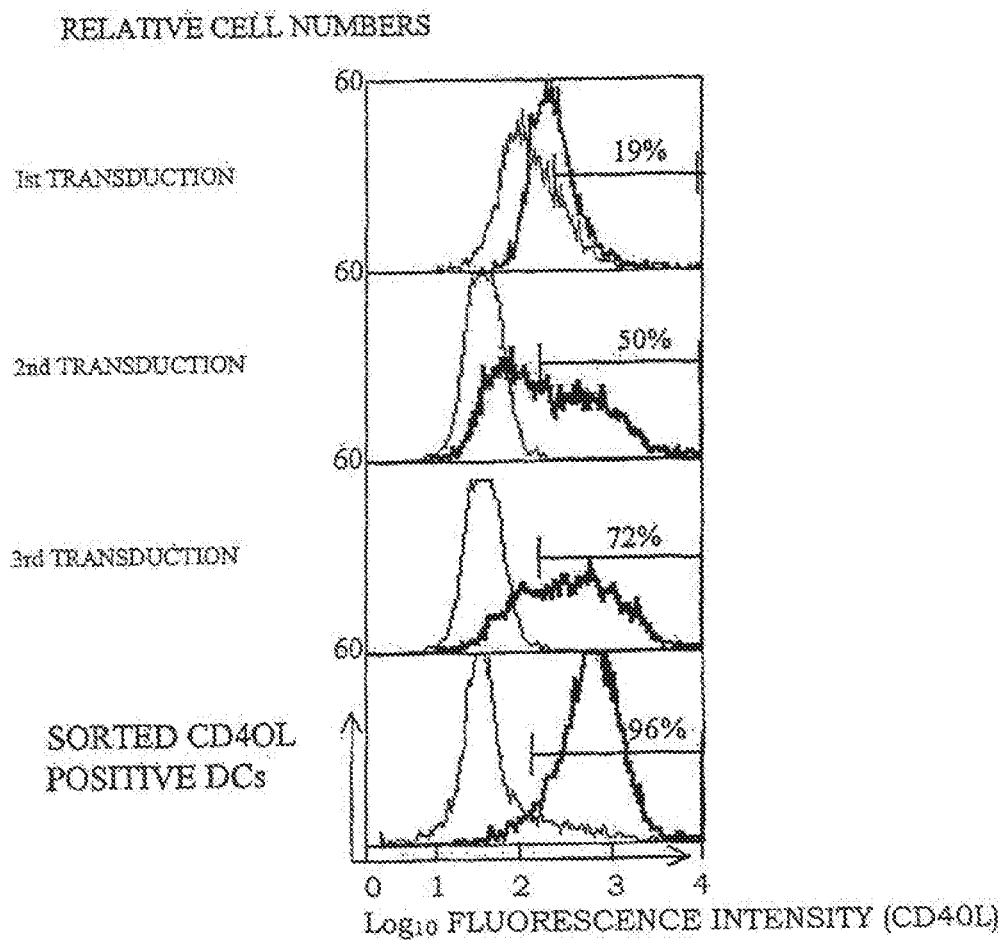
Figure 7A:
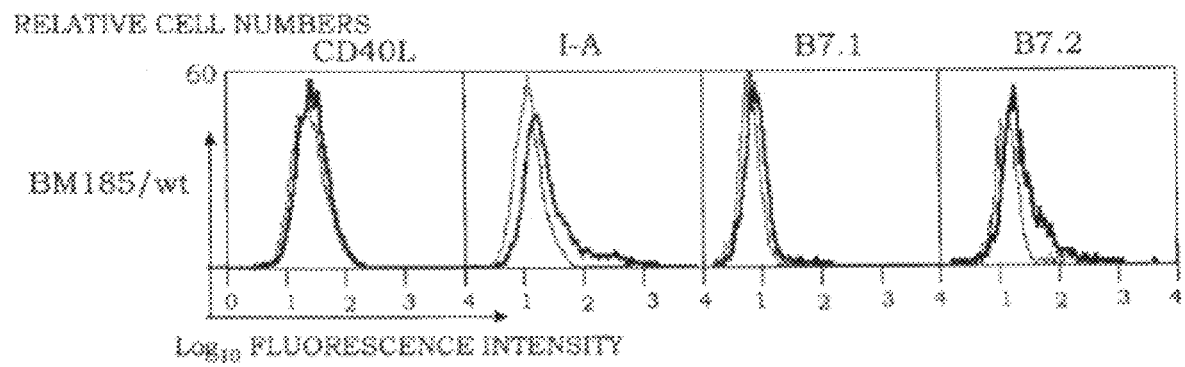
Figure 7B:
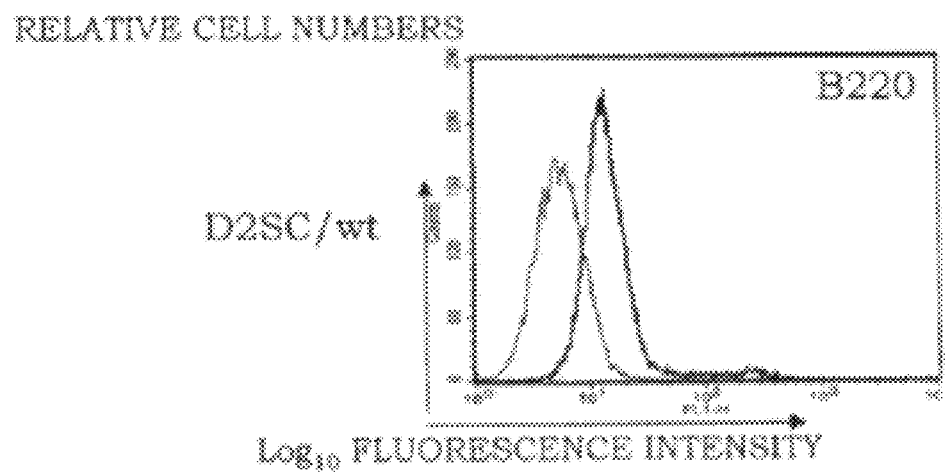
Figure 8:
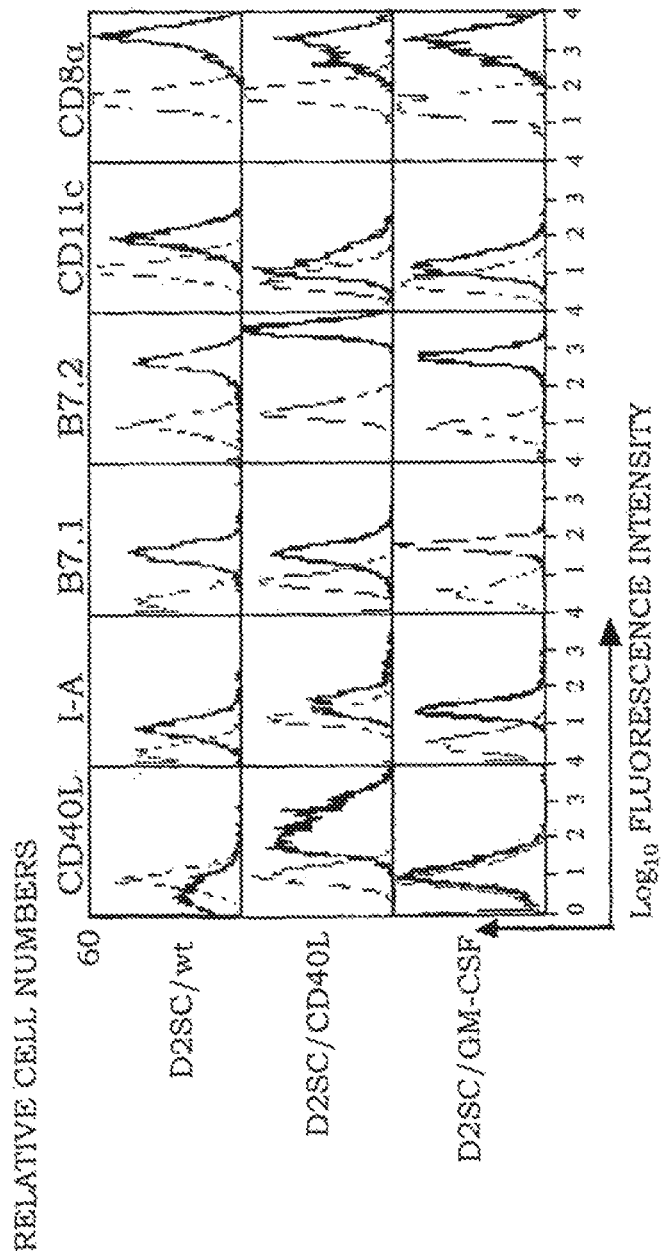
Figure 9:
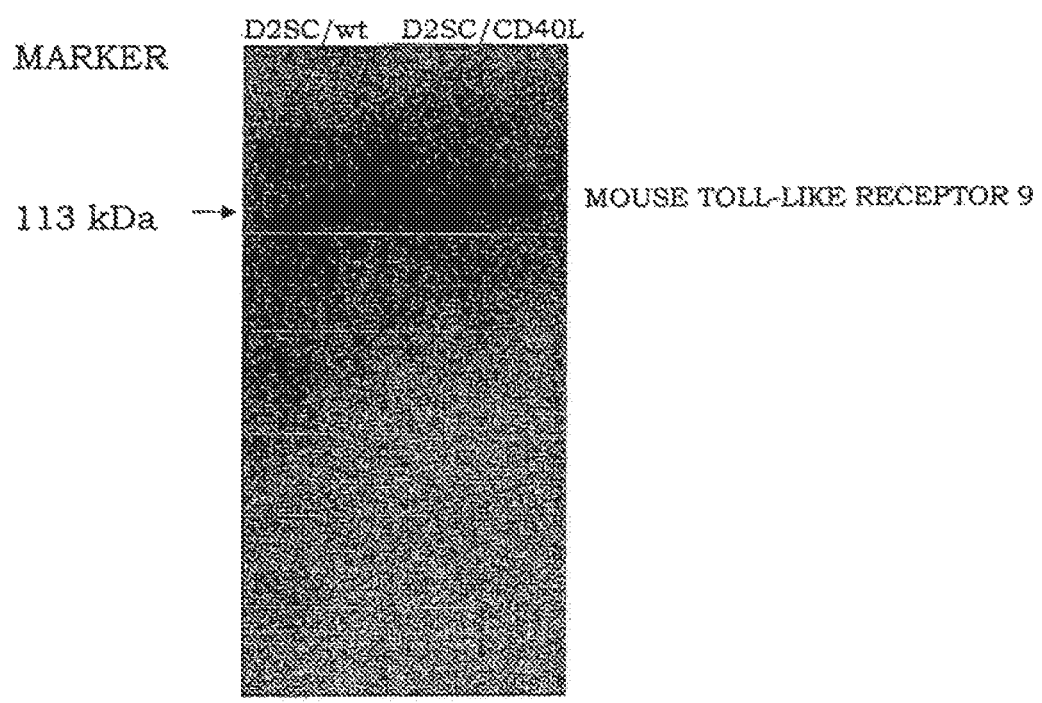
Figure 10:
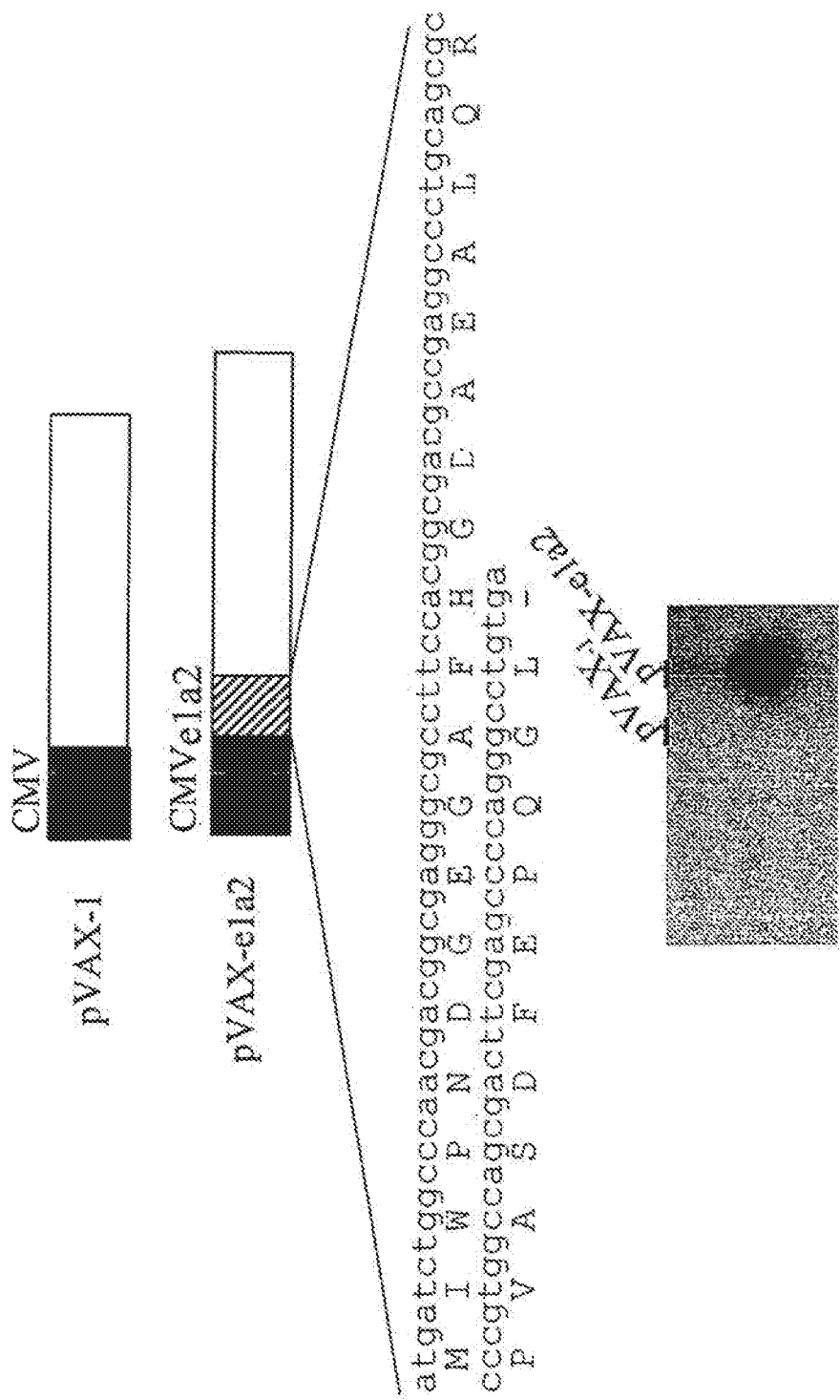
Figure 11A:
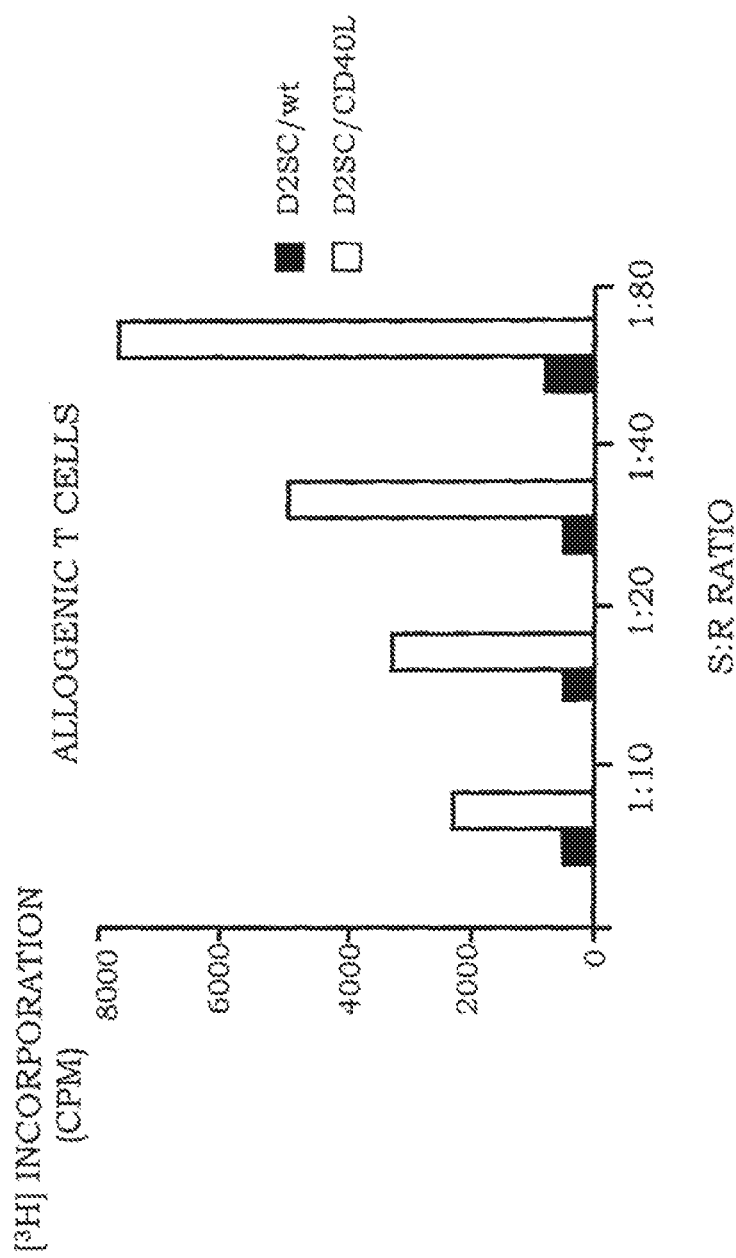
Figure 11:
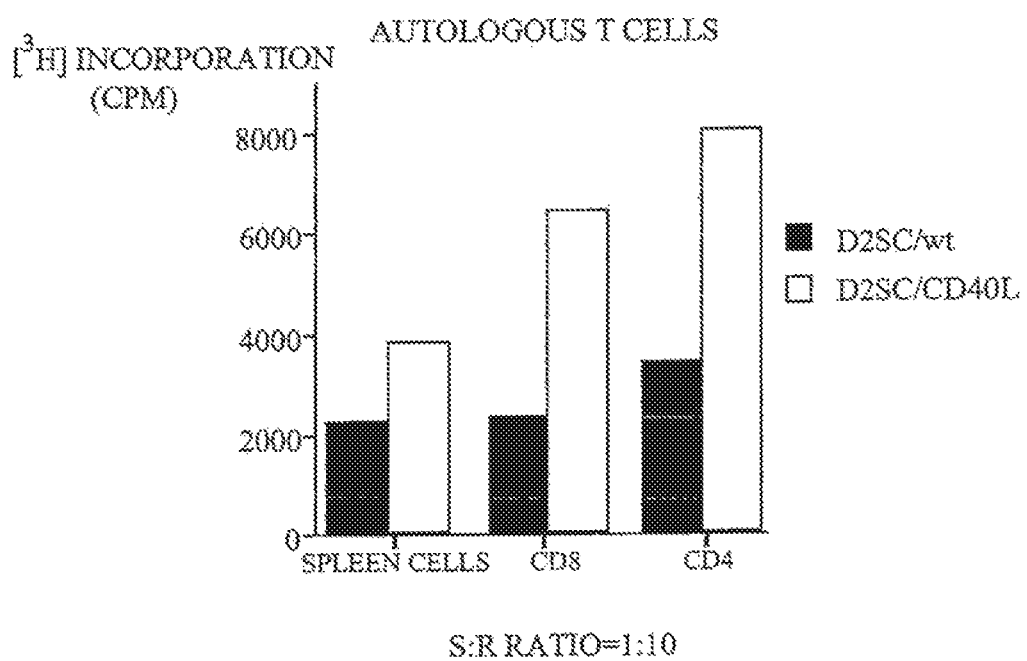
Figure 12A:
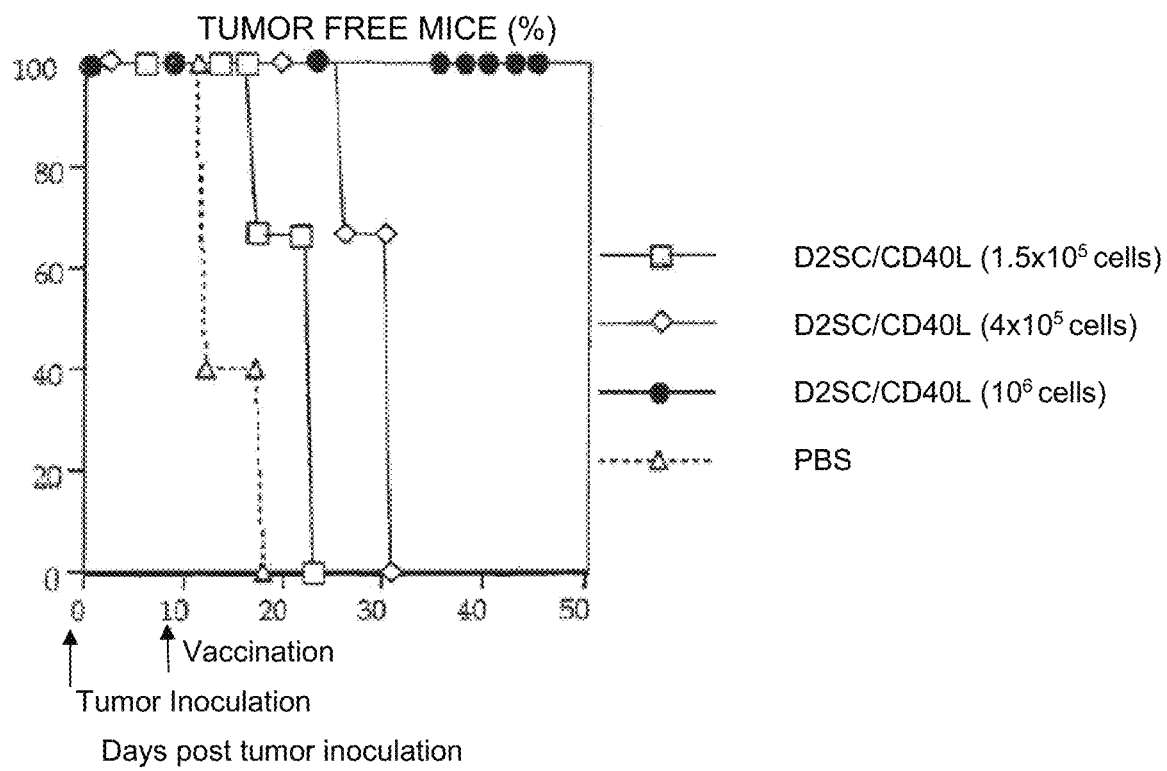
Figure 12B:
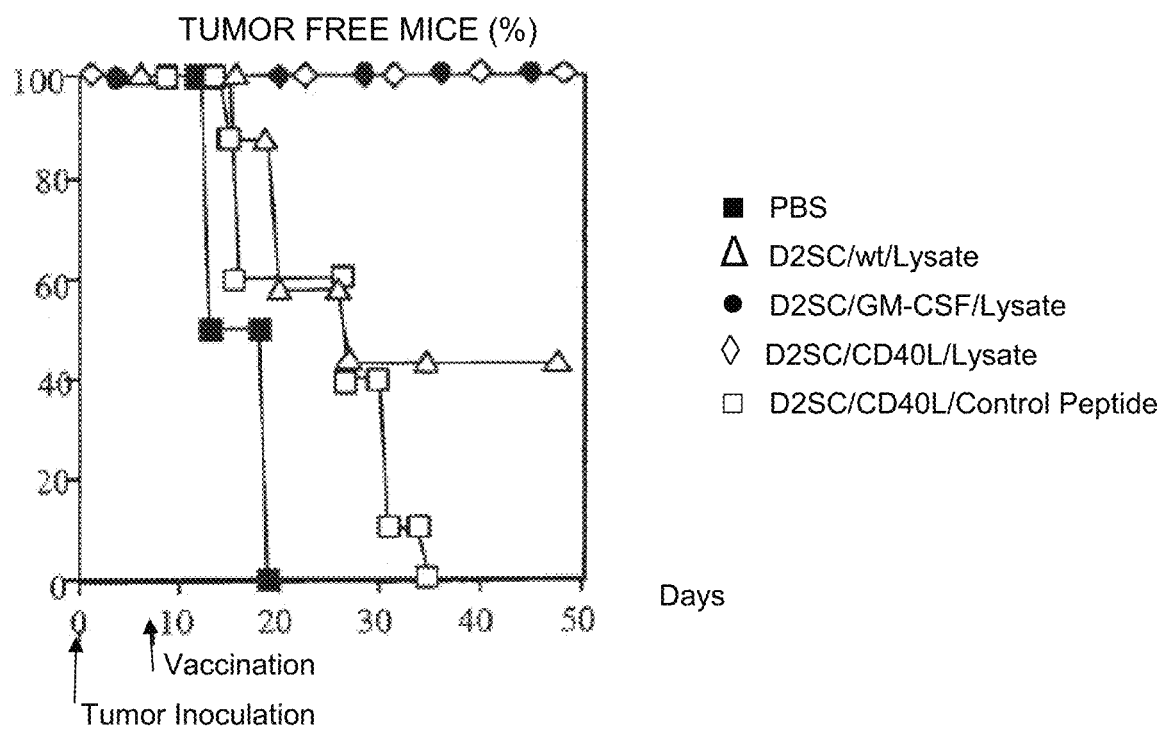
Figure 13A:
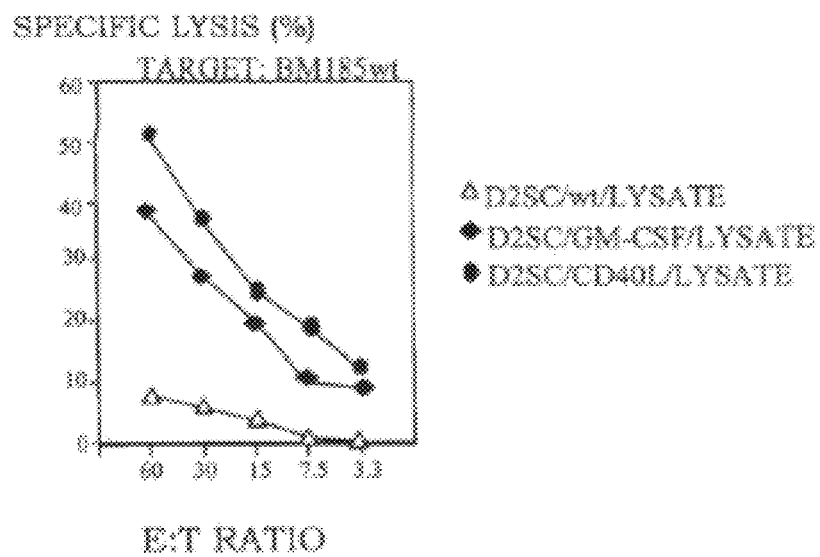
Figure 13B:
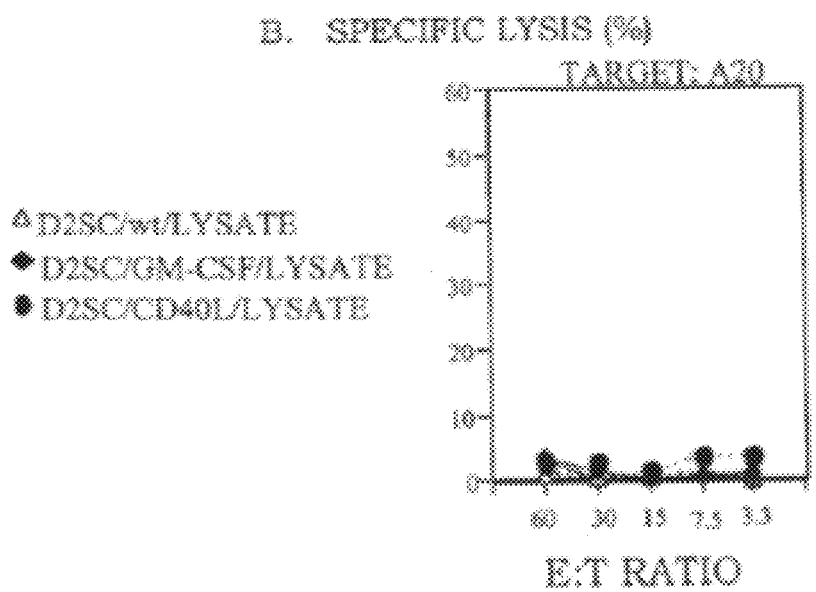
Figure 14A:
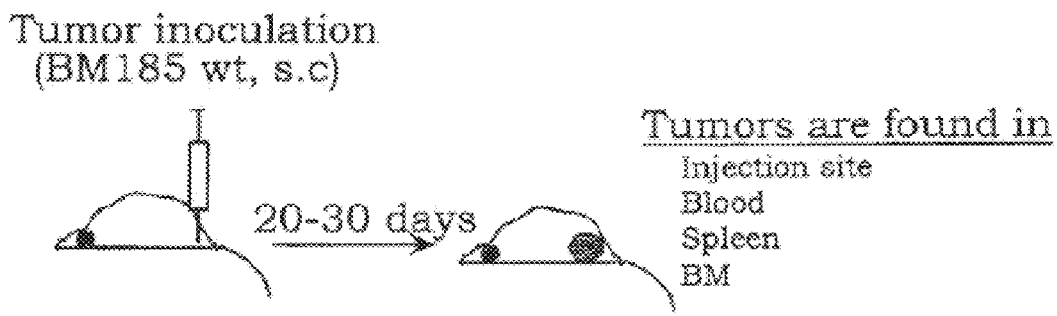
Figure 14B:
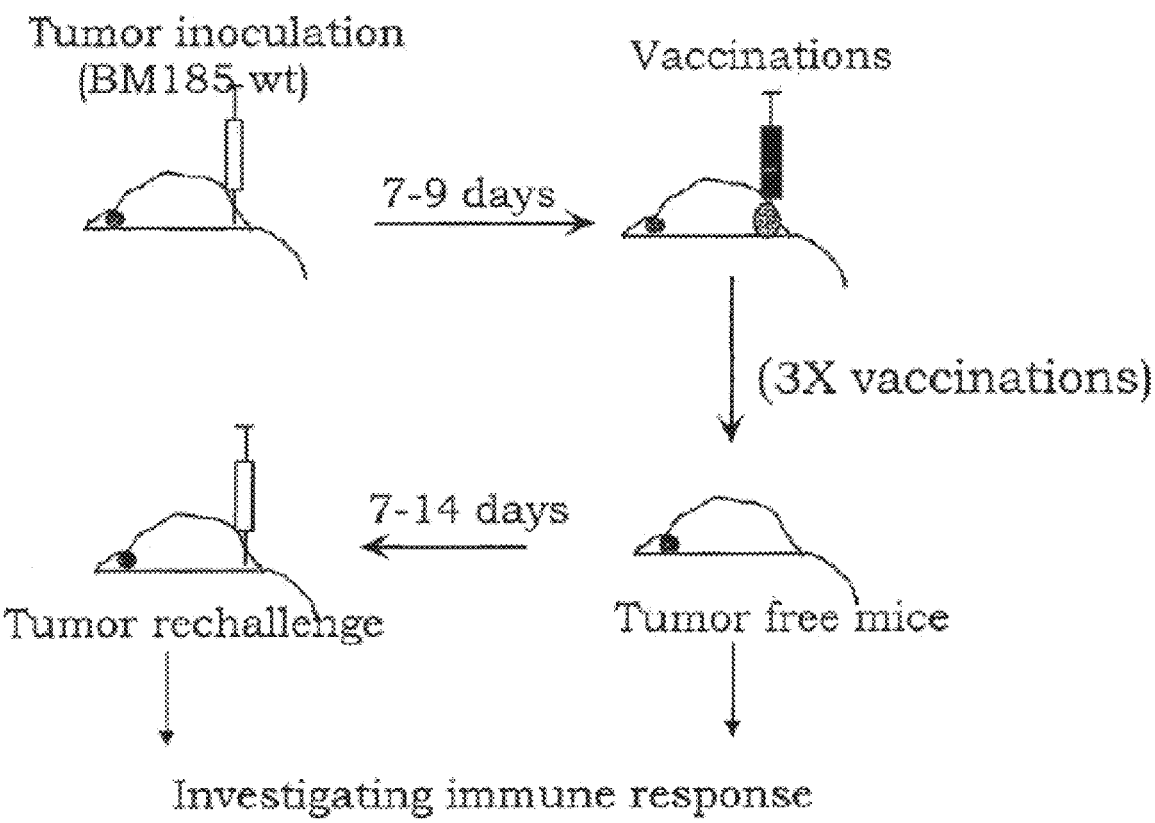
Figure 15:
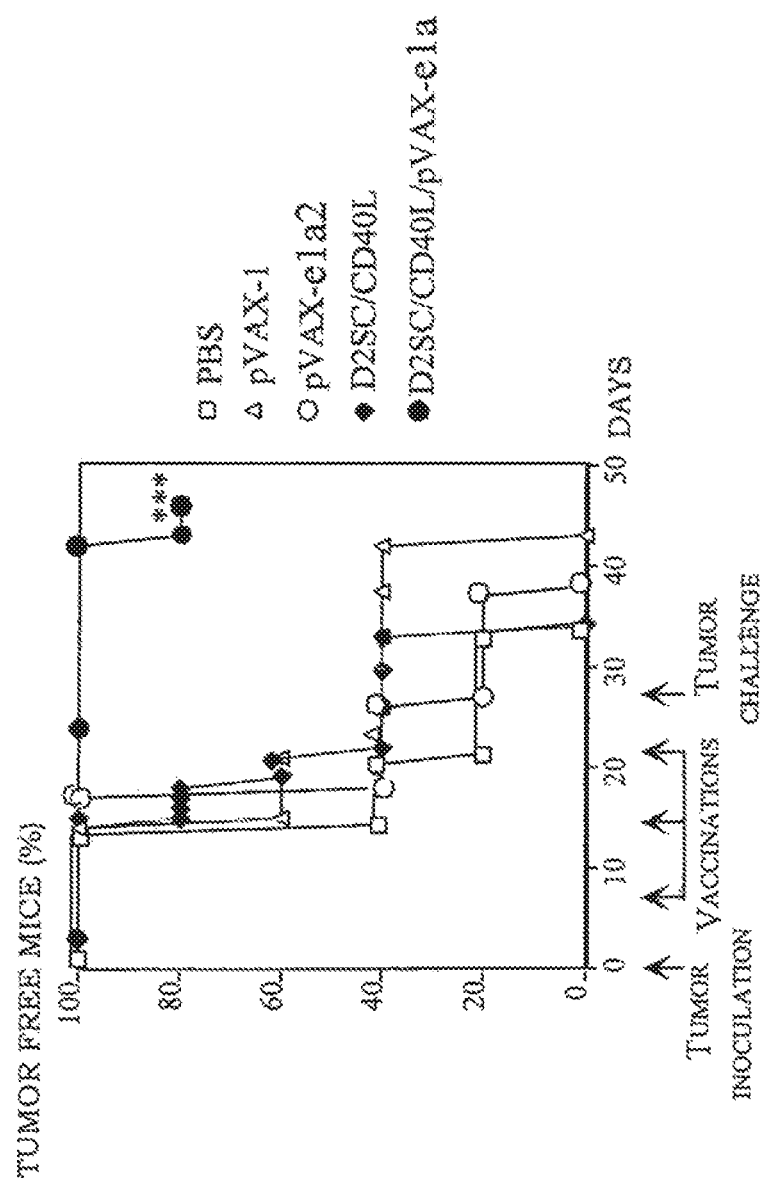
Figure 16:
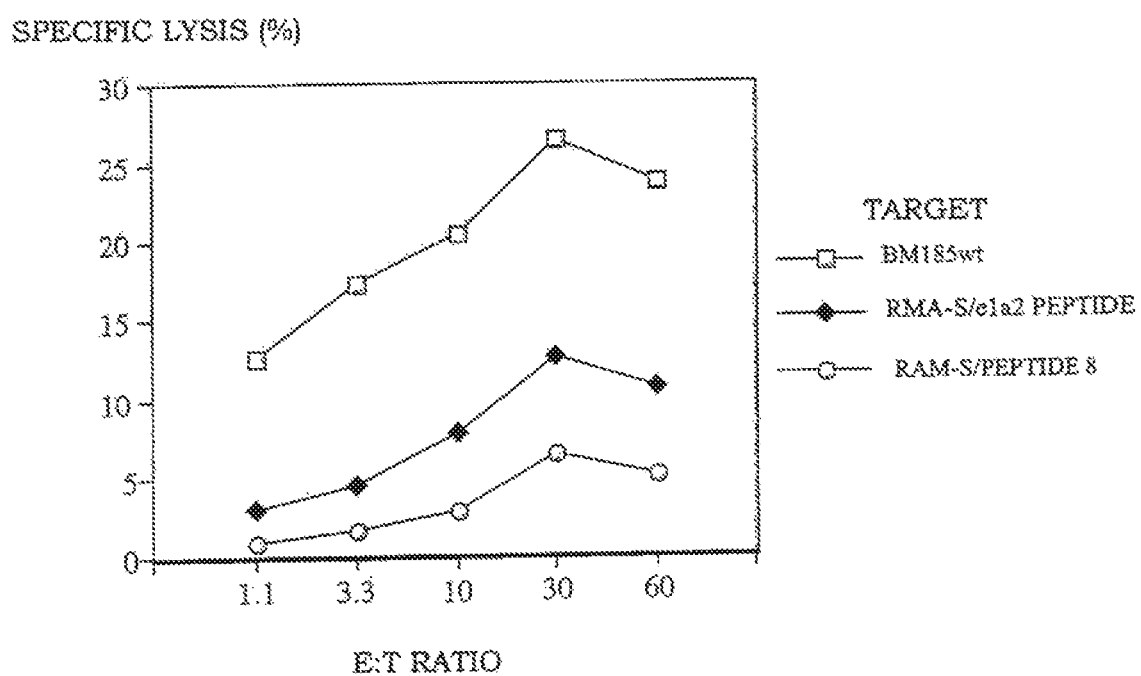
Figure 17:
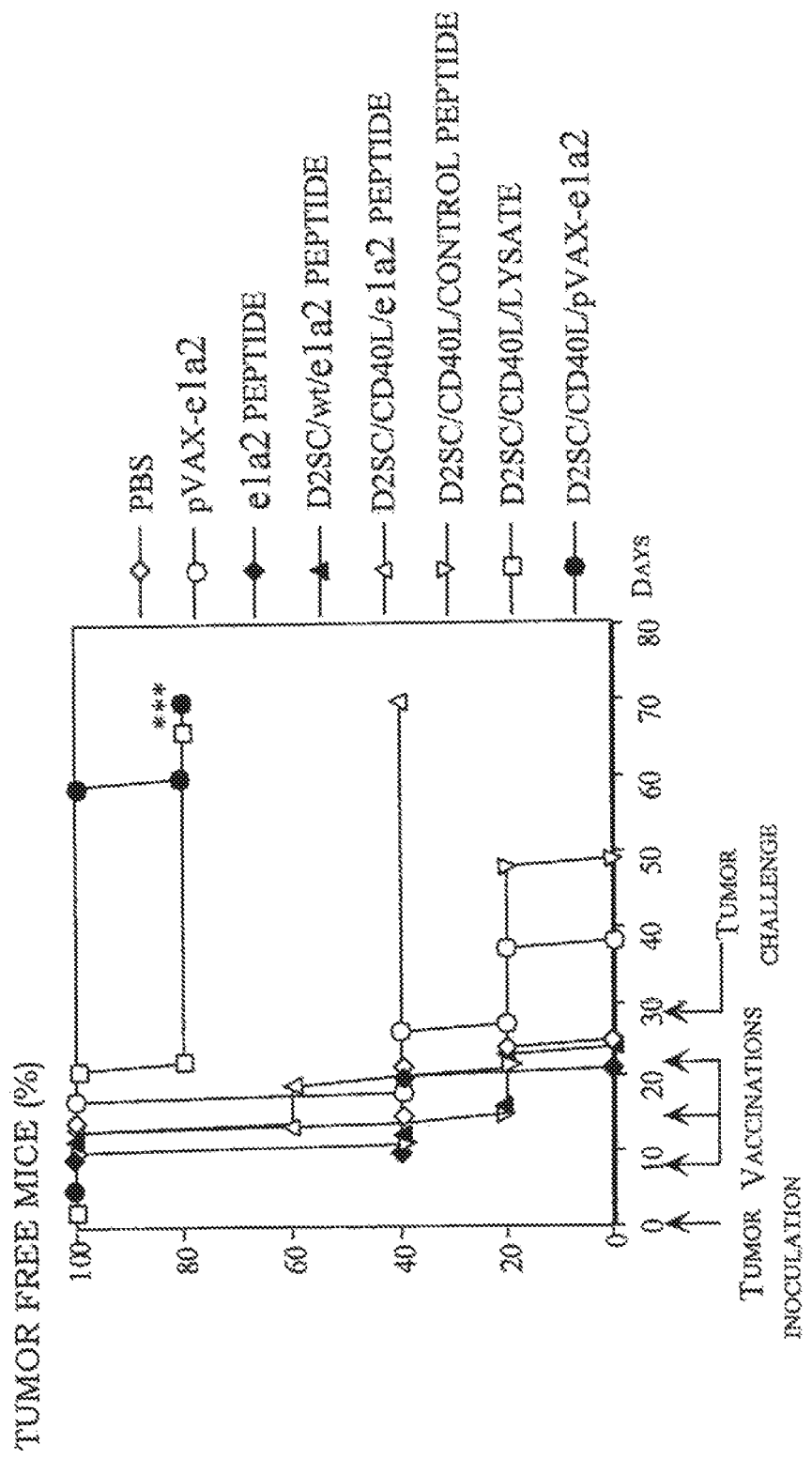
Figure 18A:
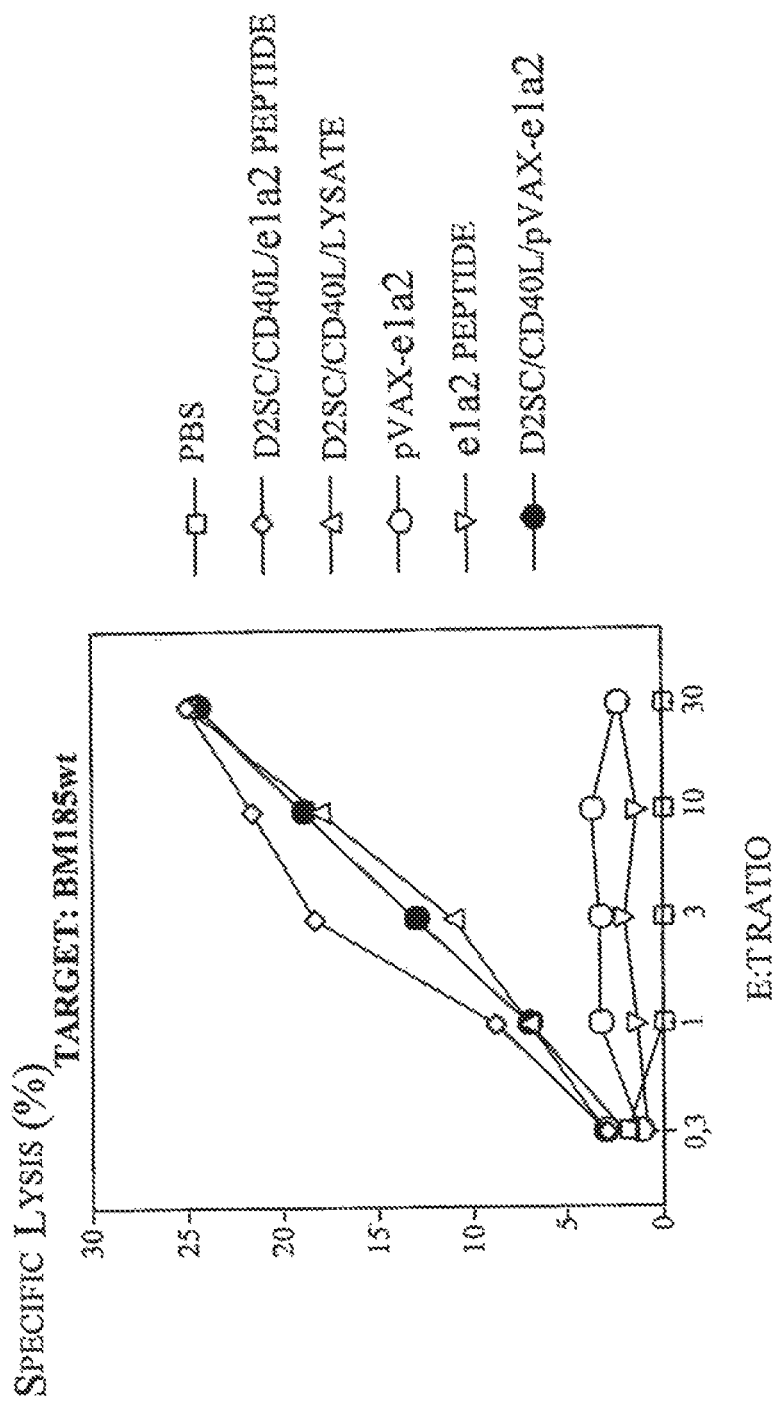
Figure 18B:
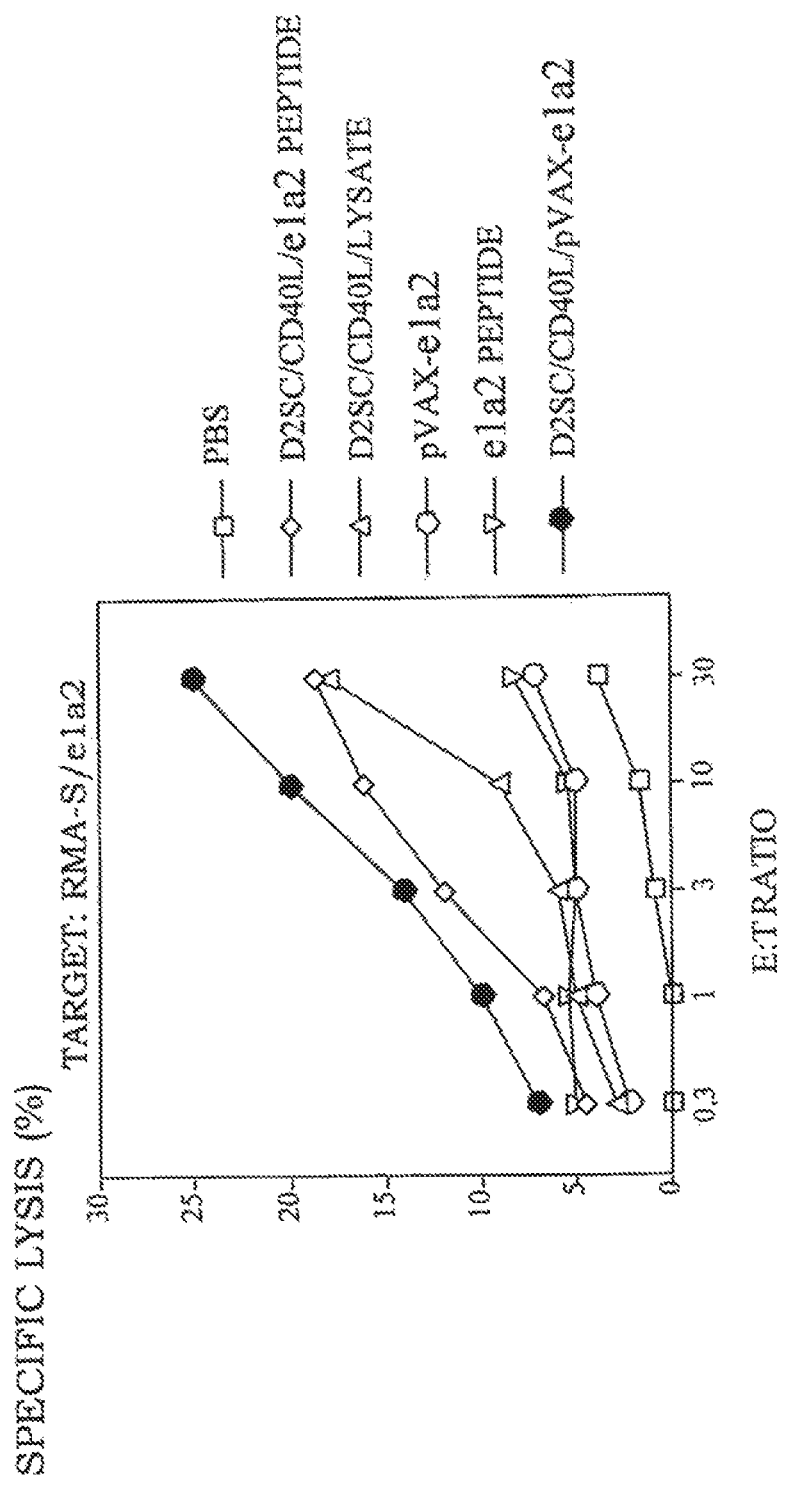
Figure 19:
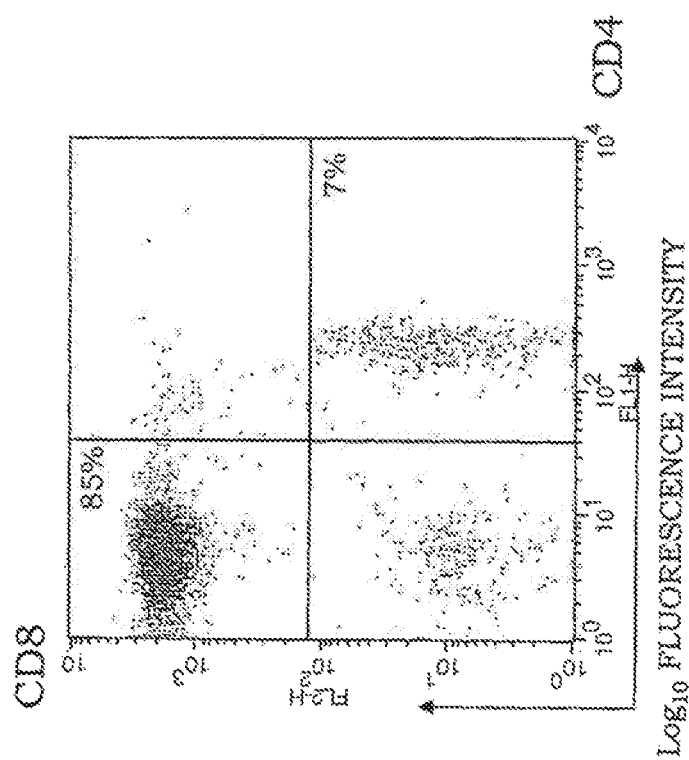
Figure 20:
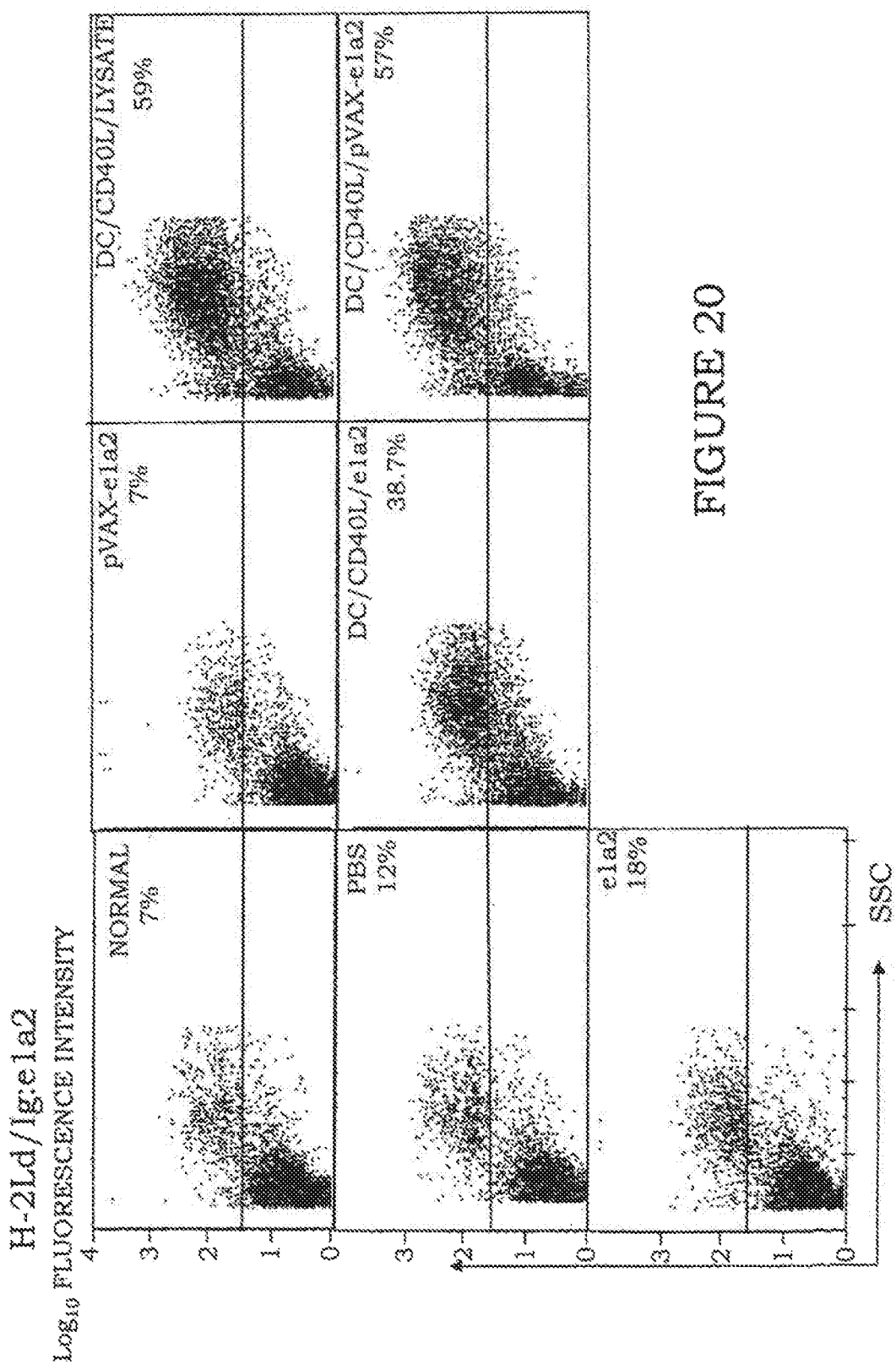
Figure 21:
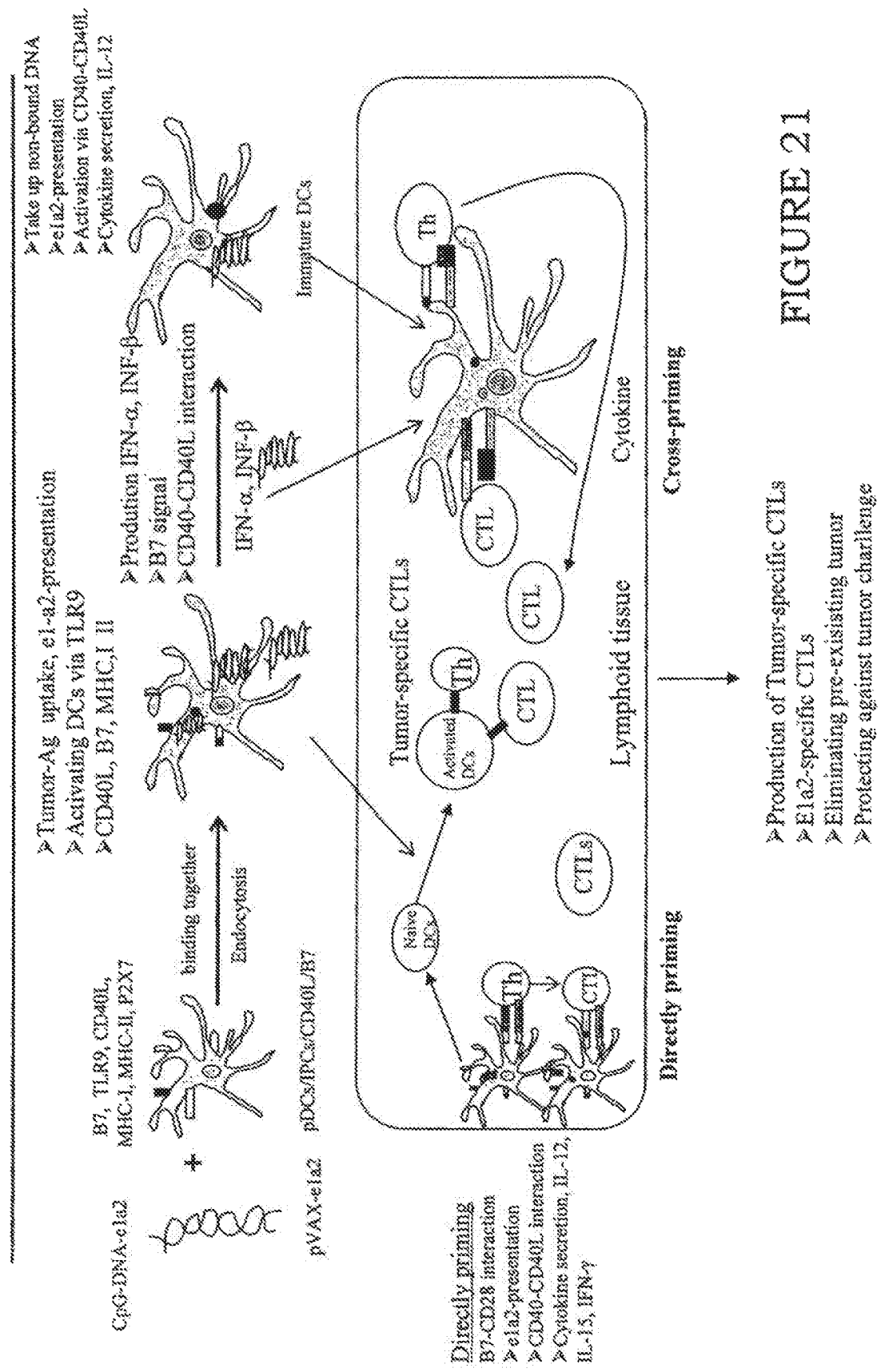

FIG. 6 illustrates transduction of DCs with RVV-mCD40L. After repeated transduction and followed by selection, DCs express readily CD40L on their surface and more than 96% of DCs express CD40L. These cells are used in an example of the vaccine composition according to the present invention;

FIG. 7A illustrates expression of immune-response stimulatory molecules in parental BM 185 wt tumor cells;

FIG. 7B illustrates expression of B220 molecule in DCs;

FIG. 8 illustrates expression of CD8a, CD11c, MHC-class II (I-A), B7.1, B7.2 and CD40L molecules in D2SC/wt, gene-modified D2SC/CD40L and D2SC/GM-CSF cells;

FIG. 9 illustrates expression of TLR9 protein in DCs detected by Western blot;

FIG. 10 schematically illustrates a portion of the empty pVAX-1 vector and a portion of the pVAX-e1a2 vector comprising a minigene sequence spanning the fusion region of human e1a2. In addition, the figure illustrates detection of the protein product of the minigene sequence by in vitro transcription-coupled translation assay of the plasmid vectors pVAX-1 and pVAX-e1a2;

FIG. 11A illustrates the capacity of D2SC/wt and D2SC/CD40L to induce allogenic T cell proliferation. A 8-fold stronger allogenic T cell proliferation is induced by gene-modified DCs compared to non-modified parental DCs;

FIG. 11B illustrates the capacity of D2SC/wt and D2SC/CD40L to elicit autologous T cell proliferation, resulting in a 4-fold stronger autologous T cell proliferation is induced by gene-modified DCs compared to non-modified parental DCs;

FIG. 12A illustrates titration of the optimal dose of gene-modified DCs used for vaccination, where the DCs were loaded with tumor-lysate prior to injection;

FIG. 12B illustrates the treatment of tumor-bearing mice with single vaccination of gene-modified DCs pulsed with tumor-lysate antigens;

FIGS. 13A and 13B illustrate the induction of tumor-specific CTLs after single treatment with tumor-lysate alone, or gene-modified DCs pulsing with tumor-lysate in tumor-bearing mice. (A) Single vaccination with tumor lysate loaded D2SC/CD40L or D2SC/GM-CSF cells elicit tumor-CTLs that can kill specifically parental BM185 wt tumor cells. (B) Noteworthy, the tumor-CTLs do not kill syngenic A20 lymphoma;

FIGS. 14A and 14B schematically illustrate an example of a mouse vaccination model employed by the present invention;

FIG. 15 illustrates the percentage of tumor free mice after administration of different vaccine compositions to mice with pre-existing bcr/abl positive tumors. Tumor free mice were further rechallenged with live parental tumor cells to examine the efficacy and specificity of induced immune protection;

FIG. 16 illustrates the induction of tumor-specific and e1a2-specific CD8+ T cells evoked by vaccination with pVAX-e1a2 and DC/CD40L;

FIG. 17 illustrates a comparison of the vaccine composition of the present invention with other vaccine compositions in treating mice with pre-existing bcr/abl positive tumors;

FIG. 18A illustrates the in vivo induction of tumor-specific T cells response after the immunization with different vaccine strategies. CTLs 30 generated from tumor free mice are specifically directed against parental tumor cells, BM 185 cells;

FIG. 18B illustrates the in vivo generated tumor antigen specific T cell response after different vaccine compositions. The in vitro cultured CTLs from tumor free mice, recognizing the e lag-peptide loaded on the TAP-deficient RMA-S cells;

FIG. 19 illustrates the percentage of CD8+ CTLs generated after in vitro T cell expansion;

FIG. 20 illustrates the e1a2-peptide specific CD8+ T cells recognize the e1a2 peptide loaded with H-2L$^d$:Ig complex and;

FIG. 21 illustrates a proposed hypothesis on the mechanisms that may govern the effects of present invention.

DETAILED DESCRIPTION OF THE INVENTION

Unless defined otherwise, all technical and scientific terms used herein have the meaning commonly understood by a person skilled in the art to which the present invention belongs. The following references provide a general definition of many of the terms used in this invention: Singleton P and Sainsbury D, Dictionary of microbiology and molecular biology, 3$^{rd}$ ed., 2002, Walker, The Cambridge dictionary of science and technology, 1988, Rieger R, et al., eds., Glossary of genetics, 5th ed., 1991, Hale W G and Marham J P, Harper Collins dictionary of biology, 1991, Abbas A, et al., Cellular and Molecular Immunology, 2003, *Blood* 2001: 1:587-600. For clarity of the invention, the following definitions are used herein.

The term "nucleotide sequence" includes, unless otherwise specified, double stranded and single stranded DNA, oligonucleotide, cDNA and RNA. Also hybrids such as DNA-RNA, DNA-DNA hybrids are included in the term. Reference to a nucleotide sequence or nucleic acid sequence can also include modified bases, related naturally occurring structural variants and synthetic non-naturally occurring analogs known to the person skilled in the art.

"Immune response" refers to a collective and coordinated response to the introduction of foreign substances in an individual mediated by the cells and molecules of the immune system.

"Immune system" refers to the molecules, cells, tissues and organs that collectively function to provide immunity or protection against foreign organisms.

"CpG-motifs" refer to the presence of unmethylated "CpG dinucleotides, or "CpG-motifs" in e.g. bacterial, yeast, insect and/or neomatode DNA. The CpG-motifs have been identified in many bacterial plasmids and they act as potential adjuvants in DNA vaccination. (*Immunol. Today* 1998, 19:89-97). CpG-DNA is now known to be a potent Th1-like adjuvant not only promoting "cross-priming" of MHC class 1 restricted CTL response to peptides or proteins but also triggers Th1-mediated antibody response. (*Immunity.* 2001 14:499-502) On the other hands, DNA sequences without CpG dinucleotides have suppressive effects on immune system. (*Arthritis and rheumatism.* 2003, 48:1701-1707)

"P2 receptors" refer receptors for extracellular nucleotides. P2 receptors are divided into two subfamilies: G protein-coupled (P2Y) and ligand-gated ion channels (P2X) (*Curr Opin Cell Biol.* 1996, 8:474-483)

"Antigen-presenting cell (APC)" refers to a cell having antigen-processing and antigen-presenting capability. These APCs display peptide fragments of protein antigens, in association with MHC molecules, on its surface, and activates antigen-specific T cells. In addition to displaying peptide-MHC complexes, APCs also express co-stimulatory molecules for optimal activation of T cells. In particular, APC refers to professional APC, including DCs, IPCs, NIPCs, monocytes, macrophages, T cells and B cells, more preferably pDCs, IPCs, NIPCs and professional APCs having pDCs/IPCs/NIPCs characteristics and functions e.g. as defined by expression of TLR9 and production or secretion of type I interferon and preferably secretion of TNF-α after stimulation by microbials.

"Modified APCs" refer to antigen-presenting cells acquiring genetic or proteomic information received by engineering or manipulation either by viral vector or by non-viral vector manipulation. As a result of the (genetic) modification, the genetic or proteomic material is introduced or incorporated into the antigen-presenting cells and expressed therein.

According to an aspect of the present invention there is provided a vaccine composition comprising an isolated or substantially purified heterologous nucleotide sequence or nucleic acid sequence coding for an antigen molecule and gene-modified antigen-presenting cells (APCs).

The vaccine composition is preferably provided as an intermixture of the nucleotide sequence and the APCs, i.e. the nucleotide sequence and the APCs are preferably pre-mixed and pre-incubated prior administration to a subject. This novel vaccine composition readily obtains enhanced immune response and superior therapeutic and protective effects compared to the prior art DNA vaccines, in particular in eliminating pre-existing cancer cells and protect the host against rechallenge of tumor cells.

The nucleotide sequence according to the present invention encodes an antigenic molecule, RNA or preferably a MHC-binding antigenic peptide/protein, that when introduced into a subject elicits an immune response against the antigen. The antigen is preferably an immunogenic molecule, an immunogenic fragment of a molecule, such as an immunogenic protein, peptide or RNA molecule or fragment thereof.

The nucleotide-based vaccine of the invention may be a univalent or multivalent vaccine. In the former of univalent vaccine, the nucleotide sequence encodes one antigen, where in the former of multivalent vaccine composition, the nucleotide sequences contain at least one heterogous gene encoding multiple antigens, either heterogous or homologous antigens. Thus, for a multivalent vaccine, several antigens are introduced and presented when administered in a subject may be resulting in activation of the antigen-specific T cells recognizing the different antigens. It can also include several copies of one antigen sequence, e.g. provided in duplicate, triplicate, etc.

The nucleotide sequence of the vaccine composition could also include other immune co-stimulating or modulating sequences, such as gene sequences encode for (protein or peptide) molecules having an immune response regulatory effects. Also co-stimulating DNA sequences, such as unmethylated CpG motifs, can be included in the nucleotide sequence.

The nucleotide sequence according to the present invention preferably, without limitation, include naked DNA or RNA administered together, preferably as a mixture, with the gene-modified APCs. If provided as a RNA sequence, the nucleotide sequence includes motifs allowing translation thereof in cells of a subject (recipient). Likewise, if provided as DNA, the nucleotide sequence includes motifs, such as promoter, possibly enhancers and/or other elements regulating transcription and translation of the nucleotide sequences.

However, the nucleotide sequences that encode for antigen, is preferably included in a vector under transcriptional control of a promoter, e.g. included in an expression cassette of vector with an expression control sequence. Furthermore, the vector or expression control sequence of the vector preferably comprises other regulatory sequences necessary and required for efficient transcription/translation of nucleotide sequence, including, but not limited to, polyadenylation sequence, transcription sequence and enhancers. The promoter or enhancer included in the vector may have the cell type specificity or tissue specificity. The promoter may be inducible or selective activated depending on the experimental design or the vaccine construction. Examples of suitable promoters for vaccination of human subjects include virus promoters, e.g. cytlomegavirus (CMV) promoter. The vector included in the present invention may be a microbial-derived vector or a non-microbial vector.

An example of a vector that could be used according to the invention is liposomes. Various cationic lipid formulations have been used for DNA delivery to cells. Insertion of polyethylene glycol derivatives into the lipid membrane or the liposomes can increase the circulation half-life of liposomes after intravenous administration.

Another class of synthetic vectors that have been actively studied is cationic polymers. The general principle is based on complex formation between positively charged polymers and negatively charged DNA molecules. Compared with cationic lipids, cationic polymers are more efficient in condensing DNA. Examples of polymers evaluated for gene delivery are poly-L-lysine, polyethylenimine (PEI) and polyglucosamines and polylipid.

Also small particles, such as nanoparticles, can be used as a vector according to the invention.

A presently preferred vector according to the invention is a DNA plasmid vector encoding MHC-binding antigen. The back bone of plasmid DNA contains preferably immune modulating sequences or adjuvants with mitogenic activity. Noteworthy, use of bacterial DNA plasmid vectors according to the present invention, either as naked DNA or embedded in liposomes or cationic polymers, or small particles offers a further advantage. These plasmid DNA vectors may include the immunostimulatory CpG nucleotide sequences. Thus, in addition to allowing delivery and expression of an antigen of the invention in a subject, the plasmid vector could stimulate the immune response of the subject.

Alternatively, viral systems can be used for delivering and subsequently production of the antigenic or immune regulating molecule of the invention. Viruses are attractive vehicles for nucleotide sequence delivery since they have evolved specific and efficient means of entering host cells and expressing their genes. The main challenge for viral vector development is the safety issue. Replication defective viral vectors or replicating viral vectors are both used in gene therapy today. Gene delivery using viral vectors is referred to as transduction. To date there are at least four types of viral vectors in clinical trials: retroviruses, adenoviruses, herpes simplex virus and adeno-associated viruses. Other viruses that are under investigation include pox virus, reovirus, lentive virus, Newcastle disease virus, alphaviruses and vesicular stomatitis virus, which may also be employed as vectors to according to the invention.

The APCs of the present invention are the cell types that are specialized for processing and presenting antigens to the immune system. The APCs of the present invention are preferably professional APCs including, but not limited to, DCs, IPCs, NIPCs, macrophages, monocytes, B cells, Langherhans cells, Mast cells, T cells, bone marrow derived cells, cells differentiated from stem cells, vascular endothelial cells and/or various epithelial and mesenchymal cells. Also a mixture of at least two types of APCs can be used according to the invention. A presently most preferred type of APCs is pDCs, IPCs, NIPCs or cells having pDCs/IPCs/NIPCs characteristics, preferably as defined by expression of TLR9 and inducible production of type I IFN. These cells play important rolls in defense against microbials and they can also cross-prime T cells in a subject and acts as linkage between the innate and adaptive immune responses.

The preferred subtype of dendritic cells according to the invention, pDCs/IPCs, has a high capacity to process and present MHC-binding antigens, produces high levels type I IFN when loaded with viral or bacterial DNA, expresses P2X7 receptors and toll-like receptors, e.g. TLR9.

TLRs play important rolls in host defense against infections. TLRs recognize pathogen-associated molecules and signals responsible for the activation of host defense system, especially pro-inflammatory cytokines. TLR9 is of special importance for the present invention since the cellular response to CpG-DNA is mediated by TLR9. TLR9 is localized to the endoplasmic reticulum (ER) of dendritic cells (DCs) and macrophages. TLR9 does not trigger endocytosis of CpG-DNA but activates DCs downstream of endosytosis.

Thus, the APCs included in present invention are preferably selected from such pDCs or other APCs having the above-listed properties and functionalities.

The APCs of the vaccination composition according to the present invention are (genetically) modified APCs. Thus, the APCs are modified to express molecules that modulate, i.e. enhance or suppress or induce tolerance or allergy of immune response, induce apoptosis and/or other cell-survival modulating responses depending on the design or vaccination strategy. The APCs may be modified to increase antigen process and presentation, activate the APCs and/or enhance the immune function of effector cells. Thus, genetic material has been introduced or transferred into the APCs for either transiently expression from an episomal location or stably expression when integrated into the host genome of the APCs or provided as a stable extra-chromosomal element. Suitable genes used for modifying APCs include cytokine genes, interleukin genes, adhesion molecules, interferon genes (e.g. type I IFN-α and IFN-β), chemokine genes, chemokine receptor genes, anti-apoptosis genes and genes encoding different immune co-stimulating molecules, immune regulating molecules, ligands (e.g. CD40L) and receptors as well as pharmaceutically accepted carriers.

For example, CD40 ligand plays important role in participating adaptive immune response. CD40 has emerged as a key signaling for the function of B cells, monocytes, and DCs. CD40L (CD154) is expressed in activated T cells after antigenic stimulation and costimulation with DCs. CD40-CD40L interaction induces activation and differentiation of DCs. Upon on CD40-CD40L activation, DCs acquired the capacity to induce production of high levels of the cytokine IL-12, which polarizes CD4+ T cells toward a Th1 type, enhances proliferation of CD8+ T cells and activates NK cells. Thus, CD40-CD40L interaction functions in the adaptive immune response as a trigger for the expression of co-stimulatory molecules and for the efficient T-cell activation. Thus, the APCs of the invention could then be genetically modified to provide the efficient expression of CD40 and/or CD40L.

Suitable gene delivery protocols for modifying APCs include, without limitation, viral and non-viral methods. Examples of usable viral vectors include, without limitation, retrovirus, adenovirus, adeno-associated virus, vaccina virus, herpes simplex virus and lentvirus. Non-viral delivery of gene into APCs includes, without limitation, plasmid DNA transfection, liposomes, electroporation, microinjection and microbial-originated vectors and toxin-derived from microbials.

Furthermore, the APCs preferably also express other cell-surface molecules including, without limitation, adhesion molecules and co-stimulatory molecules, which are required for efficient the activation of T cells and other types of immune cells. In addition, the APCs of the present invention preferably express chemokines and chemokine receptors and FLIt 3 ligand.

In an embodiment, the APCs of the present invention can be obtained from a subject, preferably without limitation, the same subject to whom the vaccination composition is given, i.e. autologous APCs are used. Alternatively, alleogeneic APCs can be included or syngeneic APCs (from an identical twin of the subject).

In another embodiment, the APCs can optionally be enriched or purified and/or expanded ex vivo or in vivo by methods well known in the art. For example, without limitation, in the presence of cytokines, the APCs are obtained by activating and differentiating stem cells and progenitor cells derived from peripheral blood, cord blood or bone marrow.

In a further embodiment, the vaccine composition is provided as pre-treated mixture comprising the nucleotide sequences encoding foreign antigen and the gene-modified APCs.

After APCs take up or endocytose the nucleotide sequences, the nucleotide sequences are processed. The CpG-motifs preferably included in nucleotide sequences activate the toll-like receptor pathway in APCs and stimulate production of type I IFN-α and IFN-β and present the encoded antigene(s). This event may occur during the incubation of the nucleotide sequences and the modified APCs prior to administration of the vaccine composition. Thus, after the pre-incubation, the modified APCs, presenting the MHC-binding antigen and expressing or secreting immune co-stimulating molecules, can either directly or indirectly activate naive APCs in the subject administered by the vaccine. The modified APCs used in the invention may then migrate to lymphoid organs and can directly or indirectly prime naive T cells, B cells and DCs, thereby obtaining a faster, increased and more efficient therapeutic and protective immune response against the foreign antigen.

Thus, the mixing of nucleotide sequence and modified APCs according to the invention is a preferred and novel step in obtaining the high efficiency of the vaccine composition.

Furthermore, once injected into a subject, the nucleotide sequence or nucleotide-sequence-comprising vector will be taken up by the subject's cells and expressed therein. Subsequently, the synthesized antigen molecule is processed in the cytosol into peptides by proteasomes.

Furthermore, after vaccine administration, professional APCs either directly acquire antigen or take up antigens released from other transfected cells. Lysis of cells transfected with vector or nucleotide sequence of the invention leads to release of encoded antigen, which is taken up by APCs.

The nucleotide sequence encoding the antigenic molecule and (genetically) modified APCs of the vaccine composition are provided and administered in an isotonic, preferably buffered solution, or pharmaceutically accepted solutions, gels, suitable for use in administration to a subject, preferably a human subject. An example of such a solution is a phosphate-buffered saline (PBS) solution.

The vaccination solution of the invention may comprise additional molecules besides the nucleotide sequence and APCs. Such additional molecules could include molecules that modulate (enhance or suppress) the immune response of a subject, increase antigen presentation of APCs, stimulate secretion of Th1 or Th2 cytokines, activate the APCs, Langerhans cells, effector cells and/or enhance the immune function of APCs. Included are cytokines, adhesion molecules, heat shock proteins and chemokines, such as interleukin-1 (IL-1), IL-2, IL-4, IL-6, IL-12, TNF a, granulocyte-colony stimulating factor (G-CSF), macrophage-colony stimulating factor (M-CSF), granulocyte-macrophage-colony stimulating factor (GM-CSF), IFN γ, type I IFN-α, IFN-β, heat shock protein (hsp) 70, hsp90, gp96, CD40L and B7, carriers and adjuvants.

The solution may also comprise adjuvants or carriers modulating the immune response, increasing the antigen presentation, redirecting the vaccine to the immune system and/or facilitating DNA entry into cells. Adjuvants include, without limitation, mineral salt adjuvants or mineral salt gel adjuvants, particulate adjuvants, toxins, microparticulate adjuvants, mucosal adjuvants and immunostimulatory adjuvants. Examples of adjuvants include aluminium hydroxide, aluminium phosphate gel, Freund's complete adjuvant, Freund's incomplete adjuvant, bacterial super-antigen, squalene or squalene oil-in-water adjuvant formulations, biodegradable and biocompatible polyesters, polymerized liposomes, triterpenoid glycosides or saponins, N-acetyl-muramyl-L-threonyl-D-isoglutamin, LPS and monophosphoryl lipid A and inactive microbes.

Another onject of the invention is use of a vaccine composition for producing an immune response in a subject. In such a case, a vaccine composition, which comprises a nucleotide sequence encoding an antigenic molecule against which an immune response is desired to be induced, and gene-modified APCs, is administered to the subject, preferably a mammalian subject and more preferably a human subject.

A further aspect of the invention is a method of treating and/or preventing a disease in a subject, preferably a mammalian subject and more preferably a human subject, by administering an effective amount of a vaccine composition according to the invention to the subject in need thereof.

The present invention also refers to a vaccine composition comprising a nucleotide sequence encoding an antigen and gene-modified APCs for use as a medicament. In another embodiment, the invention teaches the use of a vaccine composition for the manufacture of a medicament for treating or preventing an infectious disease, wherein the nucleotide sequence encodes an antigen associated with an infectious agent involved in the disease. Yet another embodiment relates to the use of a vaccine composition for the manufacture of a medicament for treating or preventing cancer, wherein the nucleotide sequence encodes a tumor-associated antigen expressed by cancer cells.

Infectious diseases to be treated or prevented by usage of a vaccine composition of the invention are caused by infectious agents including, but not limited to, viruses, bacteria, fungi, protozoa and parasites. In either way, the nucleotide sequence of the vaccine composition is coding for an antigenic molecule associated with the pathogenic microorganism causing or otherwise involved in the disease. Furthermore, this antigenic molecule is preferably recognized as non-self by the immune system of the subject to be vaccinated.

Viral diseases that may be treated or prevented by the vaccine of the invention include those caused by adenovirus, arbovirus, coxsackie virus, cytomegalovirus, echinovirus, echovirus, hantavirus, hepatitis A virus, hepatitis B virus, hepatitis C virus, herpes simplex I virus, herpes simplex II virus, Aujeszky's disease virus (ADV), human immunodeficiency virus type I and II (HIV env protein could be used as antigenic molecule), influenza (NP antigen could be used as antigenic molecule), measles virus, mumps virus, papilloma virus, papova virus, polio virus, respiratory syncytial virus, rhinovirus, rinderpest, rotavirus, rubella virus and varicella.

Examples of infectious diseases caused by *Legionella*, mycobacteria (hsp65 antigen can be used as antigenic molecule of *Mycobacterium tuberculosis*), *Mycoplasma*, *Neisseria* and *Rickettsia* bacteria may be prevented and/or treated by the vaccine composition of the invention.

Protozoa caused diseases that may be treated by the vaccine composition of the invention are diseases caused by kokzidioa, *Leishmania* and *Trypanosoma*. Whereas corresponding parasitic diseases could be caused by *Chlamydia*, the malaria parasite, *Rickettsia* and *Leishmania major* murine infection (antigenic molecule could be the LACK antigen).

The vaccine composition of the invention is also well adapted for use in preventing and/or treating cancers. The nucleotide sequence of the vaccine composition then encodes tumor-associated antigenic molecule in particular cancer type.

Several cancers are characterized by gene or chromosome translocations in the cancer cells. Such translocations could result in connecting two or more coding sequences, or portions thereof, substantially giving hybrid or fusion proteins or polypeptides. Such a resulting hybrid protein can be recognized as non-self by the patient's immune system and, thus, could have antigenic properties. One of the best-characterized examples in which a translocation creates a hybrid oncogene is provided by the Philadelphia ($PH^1$) chromosome translocation presented in patients with chronic myelogenous leukemia (CML) and acute lymphoblastic leukemia (ALL). Translocation between chromosome 22 and chromosome 9 generates Philadelphia chromosome that synthesize bcr-abl fusion transcripts. In ALL the breakpoint in bcr gene occurs in the first intron and generates e1a2 fusion gene and produce a 185 kDa tyrosine kinase with oncogenic activity. In addition, many cancers are characterized by abnormal expression of certain genes and gene products. Tumor-associated are expressed not only by tumor cells but also by normal host tissue. In order to induce an effective antitumor immune response, the vaccination must overcome the immunological tolerance of the self-antigens. One alternative approach according to the invention is to use a xenogenic source of antigen, e.g. a DNA plasmid vector, in which the nucleotide sequence encoding the tumor-associated antigen is provided, to break the tolerance of the corresponding self-antigen and to induce tumor immunity. In addition, the immune system contains autoreactive T and B cells that are not necessarily deleted from the immune repertoire during development. The autoreactive lymphocytes may be triggered by cross-reactivity between species. Cross-reactive immunity to a mouse self-antigen can be induced by immune recognition of the corresponding human protein following xenogenic DNA immunization. Thus, for obtaining an immune response in a subject, a nucleotide sequence encoding a self-antigen is preferably provided in a xenogenic vector, e.g. a xenogenic DNA plasmid vector that comprises xenogenic sequences, heterogous gene sequences, foreign gene sequences and preferably encodes xenogenic proteins and peptides in order to break the tolerance of the self-antigen.

Non-limiting examples of tumor-specific or tumor-associated antigens, the coding sequence of which may be used in the vaccine composition of the invention, include KS ¼ pan-carcinoma antigen, ovarian carcinoma antigen (CA125), prostatic acid phosphate, prostate specific antigen, melanoma-associated antigen p97, melanoma antigen gp75, high molecular weight melanoma antigen, the MAGE family of antigens, T cell receptor γ chain alternate reading frame protein (TARP) antigen, prostate specific membrane antigen and e1a2 fusion protein antigen and bcr/abl fusion protein.

Cancer vaccines for treatment of melanoma, pancreatic carcinoma, breast cancer and prostate cancer are presently used in clinical trials. The vaccine composition of the invention could then be used for these cancer types with superior results compared to the present prior art cancer vaccines. Further non-limiting examples of cancers that may be treated and/or prevented by usage of the vaccine composition of the present invention are the following types of cancer: human sarcomas and carcinomas, e.g. fibro sarcoma, myxosarcoma, liposarcoma, chondrosarcoma, osteogenic sarcoma, chordoma, angiosarcoma, enotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma and retinomblastoma, leukemias, e.g. acute lymphoblastic leukemia (ALL), and acute myelocytic leukemia (myeloblastic, promyelocytic, myelomonocytic, monocytic and erytholeukemia), chronic leukemias (chronic myelocytic leukemia, chronic granulocytic leukemia and chronic lymphocytic leukemia), polycythemia vera, lymphoma (Hodgkin's disease and non-Hodgkin's disease), multiple myeloma, Waldenström's macroglobulinemia, heavy chain disease and virus-induced cancers.

The vaccine composition of the invention can be employed for eliminating pre-existing tumors or pathogens, for treating cancer or an infectious disease. However, the vaccine composition can also or alternatively be used to protect a subject, preferably a mammalian subject and more preferably a human subject, against disease encounter or protect against a challenge or relapse with tumor cells or the pathogenic infectious agent (microorganism). In such a case, the vaccine is used for preventing cancer or an infectious disease, for example, having prophylactic properties.

Different forms of allergies and hypersensitivities may be treated by the present invention by using suitable antigen-encoding nucleotide sequences in the vector. The sequence to use depends on the particular type of allergy, and can be selected by the person skilled in the art. For example, for peanut allergy, the vector could include a nucleotide sequence encoding the Arah 2 antigen.

The vaccine composition of the present invention may be modified to treating type I diabetes, without limitation, include nucleotide sequence encoding insulin, or a portion thereof. The vaccine composition could also be applied for treat patients with Alzheimer, different blood disorders, inherited diseases, transplantation-associated or -required diseases and congenital and acquired immunodeficiencies.

The vaccine composition of the present invention may be administered to a subject, preferably mammalian subject and more preferably human subject, using suitable and clinically accepted vaccination routs including, without limitation, subcutaneously, intramuscularly, intra-arterially, intravenously, intravascularly, orally, intradermally, intraperitoneually, directly injection into lymph notes and intratumor injection. The nucleotide sequence encoding the antigenic molecule and the gene-modified APCs are preferably intermixed prior the administration, i.e. administrating a mixture of the two components of the vaccine composition of the present invention.

The vaccine may be administered by any conventional means, without limitation, including syringe, trocar, catheter, electroporation, needle-free delivery, or like.

The dosage to be administered depends to a large extent on the condition and size of subject to be treated/vaccinated as well as the amount of vaccine composition administered, frequency of administration, administration route, type of therapy, i.e. treatment and/or prevention, and type of disease to be treated or vaccinated against. Regimens for continuing therapy, including site, dose and frequency may be guided by the initial response of the subject and clinical judgement. However, for treatment of cancer, preferably at least three repeated vaccinations are given. The amount of vaccine composition to be used can be determined by dose-response experiments conducted in animals by methods well known in the art.

Yet another aspect of the invention is a kit, provided for usage in the vaccination methods of the present invention. In a first embodiment a kit comprises a container including a mixture of a nucleotide sequence encoding an antigenic molecule and genetically-modified APCs. The antigenic molecule is preferably associated with a disease, e.g. infectious disease or cancer, to be treated or prevented by administering the contents of the kit to a subject, preferably mammalian subject and more preferably human subject.

In another embodiment a kit comprises a first container, including a preparation of a nucleotide sequence that codes for an antigenic molecule, and a second container, including a preparation of genetically modified APCs. Prior administration to a subject, the content of the first and second container are preferably intermixed, e.g. by adding the content of the first container to the second container, by adding the content of the second container to the first container or by adding the content of the first and second container, respectively, to a third provided mixing container. The mixture may then be incubated together prior to injection into a subject, preferably mammalian subject and more preferably human subject.

The kits of the invention comprise a vaccine composition, pharmaceutical composition to treat and/or prevent a disease or disorder, e.g. infectious disease, cancer, autoimmune disorder, allergy or diabetes. At least one of the containers of the kit, preferably the container comprising gene-modified APCs, may include additional substances and adjuvants effecting the immune response of a subject, increasing antigen presentation of APCs, activating the APCs and/or enhancing the immune function of APCs.

A further object of the invention is to provide a method to produce a vaccine composition. Referring to the flow diagram of FIG. 1, in step S1 a nucleotide sequence encoding an antigenic molecule (against which an immune response is desired to be induced) is provided. Gene-modified APCs, e.g. DCs, pDCs, IPCs, macrophages, monocytes and/or B cells are provided in step S2. In step S3, the nucleotide sequence and APCs are mixed completing the method and ending in the vaccine composition of the invention.

Figure 1:
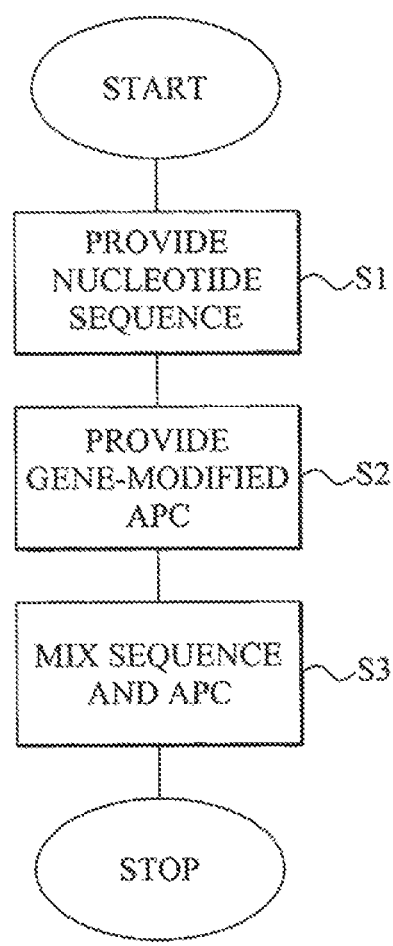
FIG. 1 is a flow diagram illustrating a method of producing or preparing a vaccine composition according to the present invention.

FIG. 2 illustrates a preferred embodiment of the nucleotide sequence-providing step S1 of FIG. 1 in more detail. In the optional step S11 the nucleotide sequence encoding the antigenic molecule associated with a disease or disorder to be treated or prevented by the vaccine composition is identified and isolated. The identification could, at least partly, be performed using MHC-binding peptide motif search, known in the art. Any methods known in the art, including chemical synthesis of DNA sequences and PCR (polymerase chain reaction), can be employed to obtain the relevant nucleotide sequence. Then in step S12 the identified and isolated nucleotide sequence is preferably cloned into a suitable vector. The vector is selected for being adapted for introduction into a subject and for, once introduced into the subject, enabling expression of the nucleotide sequence, subsequently resulting in the desired antigen molecule. The obtained vector is then propagated in step S13, e.g. in host cells, in vitro, etc.

The APC providing step S2 of FIG. 1 is illustrated in more detail in FIG. 3. In step S21, APCs are isolated, preferably from the subject that subsequently will receive the vaccine composition or from another source discussed in the foregoing. In this step S21, a particularly advantageous subclass of APC, e.g. DCs or a DC subclass, can be selected and isolated. The APCs are (genetically) engineered in step S22. In such a case, one or several genes, e.g. CD40L gene, coding for molecules that modulating immune response are introduced, either as extra-chromosomal elements or incorporated in the genome of the APCs, into the antigen presenting cells.

In the further step S31 of FIG. 4 additional substances are added to the vector-APCs mixture. Such substances could include at least one of cytokines, adhesion molecules, chemokines, heat shock proteins and adjuvants discussed previously generally modulating the immune response and immune cells of a subject receiving the vaccine composition and/or enhancing the immune function of effector cells and APCs. The mixture of nucleotide sequence and modified APCs, and possibly also additional substances, are then preferably incubated prior usage as a vaccine in the step S32. The physical conditions for the incubation can be non-inventively determined by the person skilled in the art. However, the incubation preferably lasts at least 5 minutes, more preferably at least a few hours in order to enhance the endocytosis of nucleotide sequence. An upper incubation time is typically dictated by other physical factors, such as incubation temperature. Generally, over night, i.e. up to 24 h is a suitable, but not limiting, upper incubation time limit. The temperature during the incubation is preferably at least 4° C., more preferably room temperature (about 20-25° C.) or about 37° C. The pH of the incubation solution is preferably neutral or slightly acid. In order to enhance the endocytosis, the nucleotide sequence (plasmid) and the APCs are preferably forced together using co-centrifugation. Alternatively, or addition, other techniques such as lipofectin can be used.

In the following the vaccine composition of present invention will be exemplified with reference to a vaccine against a type of acute leukemia. Thus, the antigenic molecule encoded by the nucleotide sequence is associated with that type of cancer. However, as the person skilled in the art understands the invention is not limited to this particular example of disease and antigen but can be used to treat and/or prevent any of the diseases and disorders discussed above.

EXAMPLE

The vaccine composition of present invention was compared with a variety of other approaches including vaccinations with antigenic peptide and plasmid DNA encoding antigenic peptide.

Cell Line

A20 ($H\text{-}2^d$) is a B cell lymphoma cell line derived from BALB/c mice used as a CTL target in the present invention study. A20 cells express B220, MHC-I, MHC-II and CD19 molecules.

The tumor cells (BM185 wt, $H\text{-}2^d$) is a murine acute leukemia cell line (pre-B ALL) and was established from bone marrow cells of BALB/c mice transduced with retroviral vector encoding a human 185-kDa bcr/abl oncoprotein (*Cell* 1995, 82:981-988). BM185 wt cells express B220, CD19 and MHC-I molecules on their cell surface.

D2SC/wt cells (or D2SC/1) was kindly provided by Dr. Paola Paglia. The D2SC/wt, ($H\text{-}2^d$) used in the present invention was obtained by retroviral immortalization of dendritic cells from BALB/c spleen (*J. Immunel. Methods* 1994, 174:269-279). D2SC/wt cells show most of the morphologic, immunophenotypic and functional attributes of immature DC, including constitutive expression of MHC class II molecules (low), costimulatory molecules B7/BB1, heat-stable Ag, and ICAM-1, and have an efficient Ag-presentation capacity (*J Immunol Methods.* 1994, 174:269-279., *J. Immunol.* 1999, 162(7):3757-3760).

RMA-S is a TAP2-deficient tumor cell line and was established from the Rauscher leukemia virus-induced mouse T cell lymphoma RBL-5 of B6 origin (*Nature (London)* 1986, 319:675-678).

Cell Culture

DCs were cultured in IMDM medium supplemented with 10% heat inactivated fetal calf serum (FCS) (GibcoBRL, Life Technologies Ltd., Scotland, UK), 2 mM L-glutamine, 100 IU/ml penicillin/streptomycin, 10 mM hepes and $5\times10^{-5}$ M 2-mercaptoethanol. Cells were incubated at 37° C. in a humidified atmosphere of 7% $CO_2$.

Tumor cells were cultured in RPMI-1640 medium (ICN Biomedicals, Inc. Costa Mesa, Calif.) supplemented with 10% heat inactivated FCS (GibcoBRL, Life Technologies Ltd. Scotland, UK), 2 mM L-glutamine, 100 IU/ml penicillin/streptomycin, 10 mM hepes, 0.1 mM sodium pyruvate, $5\times10^5$ M 2-mercaptoethanol and 10 mM non-essential amino acids. Cells were incubated at 37° C. in a humidified atmosphere of 5% $CO_2$.

MHC I-Binding Peptide Motif Search and Synthesis

Amino acids sequences of ALL-specific e1a2 fusion protein were used for screening of binding to mouse MHC-I antigen ($H\text{-}2K^d$) (Table I) (HLA Peptide Binding Predictions program derived from Dr. Kenneth Parker's Research, http://bimas.dcrt.nih.gov/molbio/hla_bind). A nine amino acid sequence, AFHGDAEAL, locating in the junction-region of e1a2 fusion protein (Table I and FIG. 10), was shown to have high score binding to mouse $H\text{-}2K^d$. Peptides covering the e1a2 mini-protein was synthesized by standard methods and purified by high pressure liquid chromatography (HPLC). Peptides used in the experiments were the high score binding peptide (AFHGDAEAL, see SEQ ID NO: 5 and referred to as e1a2 peptide) and low score binding peptide (HGDAEALQR, see SEQ ID NO: 6 and referred to as peptide 8). Peptide K (ATGFKQSSK, see SEQ ID NO: 7) that does not bind to $H\text{-}2K^d$ was used as control peptide.

Table I below illustrates the results from the HLA peptide motif search using the Peptide Binding Prediction program and the used user parameters, a score above 500 is regarded as a very high score binding.

TABLE I

| User Parameters and Scoring Information | |
|---|---|
| Method selected to limit number of results | explicit number |
| Number of results requested | 20 |
| HLA molecule type selected | Kd |
| Length selected for subsequences to be scored | 9 |
| Echoing mode selected for input sequence | Y |
| Echoing format | numbered lines |
| Length of user's input peptide sequence | 17 |
| Number of subsequence scores calculated | 9 |
| Number of top-scoring subsequences reported back in scoring output table | 9 |

| Scoring Results | | | | |
|---|---|---|---|---|
| Rank | Start Position | Subsequence Residue Listing | Score | Seq ID No. |
| 1 | 3 | AFHGDAEAL | 1152.000 | 5 |
| 2 | 7 | DAEALQRPV | 14.400 | 8 |
| 3 | 9 | EALQRPVAS | 2.000 | 9 |
| 4 | 2 | GAFHGDAEA | 1.440 | 10 |
| 5 | 8 | AEALQRPVA | 0.120 | 11 |
| 6 | 5 | HGDAEALQR | 0.120 | 6 |
| 7 | 1 | EGAFHGDAE | 0.100 | 12 |
| 8 | 4 | FHGDAEALQ | 0.012 | 13 |
| 9 | 6 | GDAEALQRP | 0.012 | 14 |

Genetically Modification of DCs

A gene transfer system based on retroviruses was developed. The retroviral provirus was manipulated so that all of the gag, pol and env genes are removed but the 3'- and 5'-LTRs are retained. The defective retrovirus vector was produced in the supernatant from the packaging cell line.

Figure 5A:
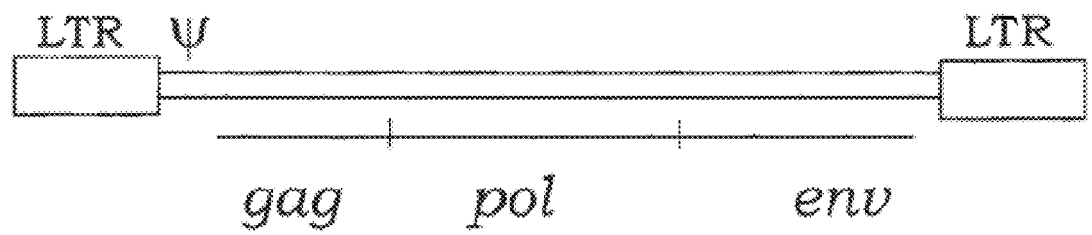
FIGS. 5A and 5B illustrate a schematic drawing of a Moloney murine leukemia virus-vector containing mouse CD40 ligand (CD40L) gene (RVV-mCD40L)
Figure 5B:
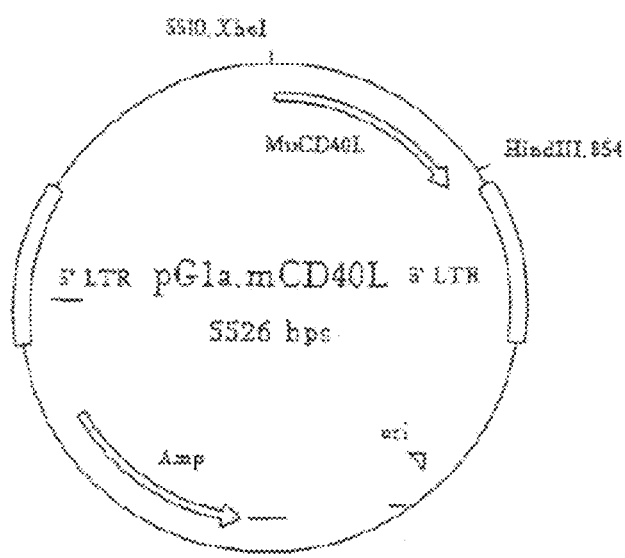

In the present invention, retroviral vectors (see FIG. 5) derived from the packaging cell lines of MFG-mGMCSF (kind gift of Dr. Richard Mulligan, Children's Hospital, Harvard Medical School, USA) and a Moloney murine leukemia virus vector (MoMLV), PG1a.muCD40L, (kind gift of Dr. M. Brenner, Baylor College of Medicine, USA) were used to modify DCs.

The DCs used in the present invention are engineered to secrete GM-CSF or express CD40L on their cell surface. The CD40L gene or GM-CSF was transferred into DCs using the muCD40L retroviral vector. D2SC/wt cells were transduced by repeated spinoculation in the presence of polybrene (10 mg/ml, Sigma). In brief, $10^5$ cells were suspended in 0.5 ml viral supernatant and polybrene. Cells and virus were co-centrifuged at 10 000 rpm, at room temperature for 60 min. After centrifugation, the supernatant was discarded and the cells were suspended in fresh medium and incubated at 37° C. in a humidified atmosphere of 7% $CO_2$ for 24 h prior to a second round of infection. The transduction efficiency of DCs was markedly enhanced by repeated centrifugation. Several rounds of transduction were performed and the corresponding percentage of cells expressing CD40L is illustrated in FIG. 6.

After repeated transduction, approximately 70-80% of DCs expressed CD40L transgene. The D2SC/CD40L cells were further sorted for the transgene expression and approximately 96% of DCs expressed the CD40L gene product. The CD40L gene expression remained stable for years and even after repeated thawing-freezing procedures. The DCs express readily CD40L on their cell surface, see bottom diagram of FIG. 6.

Cell culture supernatant of D2SC/wt, CD40L and GM-CSF transduced DCs was harvested and evaluated for IL-12, GM-CSF, IFN-γ production by ELISA according to the manufacturer's instructions (Cytoscreen™, immuneassay kit, Biosource Int., California, USA, BD Bioscience, U.S.A). GM-CSF secretion in the cell culture supernatant of D2SC/GM-CSF cells was 11 370 pg/ml/$10^6$ cells/24 h.

Immunophenotype Characterization of Tumor Cells, D2SC/Wt, D2SC/CD40L and D2SQ/GM-CSF Gene-Modified DCs Cells were incubated with mouse monoclonal antibodies ($2\times10^5$ cells/0.5 µg mAbs, BD, Pharmingen, San Diego, Calif.) against a panel of surface molecules. The following mAbs were used: CD40-FITC (fluorescein isothiocyanate conjugated mAB), CD40L-PE (R-phycoerythrin), I-A-FITC, H-2K$^d$-FITC, B7.1-FITC, B7.2-PE, CD11c-FITC, CD8a-PE, B220-FTIC, B220-PE, Thy1.2-FITC, Thy1.1-PE, IgG1-FITC, IgG2-PE. Phenotypic analysis was performed on a FACSCalibur flow cytometer (Becton Dickinson).

The immunophenotype of tumor cells (BM185/wt) is illustrated in FIG. 7A. BM185 cells express B220, CD19 and MHC-I, I-A molecules on their cell surface. However, BM185 wt cells lack expression of co-stimulatory molecules and CD40 (data not shown).

Expression of B220 molecule on D2SC/wt cells is shown in FIG. 7B. Thus the D2SC/wt cells express the markers, CD8a+, CD11c+ (see FIG. 8) and B220+ known as the characteristic markers for a subclass of DCs, plasmacytoid dendritic cells (pDCs) in mice.

The immunophenotypes of parental D2SC/wt cells and gene-modified dendritic cells (D2SC/CD40L) are compared and illustrated in FIG. 8. The parental D2SC/wt cells represent an immature DC phenotype and express MHC-1, I-A, CD8a, CD11c, B7.1 and B7.2 on their cell surface, as is illustrated in the figure, but lack of CD40 ligands expression. In comparison, readily expression of CD40L was found in D2SC/CD40L cells. However, the IL-12 secretion was not detected in D2SC/CD40L cell culture media. In vitro growth kinetics of D2SC/CD40L cells was similar to their parental cells (data not shown).

Western Blot

DCs were lysed in lysis buffer containing 1% NP40, 0.1% SDS, TBS, and protease inhibitor cocktail according to manufacture's instruction (Sigma). Cells were subsequently sonicated in lysis buffer at 4° C. After centrifugation at 5 000 rpm, 5 min at 4° C., the soluble proteins were collected and analyzed by Western Blotting. Proteins were separated on a 12% SDS polyacramide gel and transferred on a PVDF filter according to the manufacture's instruction (BioRad, USA, Amersham Bioscience, Uppsala, Sweden). The primary polyclonal antibody, rabbit anti-mouse TLR9 (Cat. No IMG-431, Imgenex, San Diego, USA) was used at a dilution of 1:1 000 in TBS buffer (10 mM Tris-Cl and 150 mM NaCl, pH 8.0). Secondary antibody was a goat anti-rabbit antibody conjugated with horseradish peroxidase (HRP). The DCs included in the invention express the mouse TLR9 receptor, which is illustrated in FIG. 9.

D2SC/wt cells are full functional immature dendritic cells isolated from spleen. It was shown that D2SC/wt cells express the well know markers, such as CD11c+, B220+, CD8α+, MHC-II$^{low}$, TLR9+ found in pDCs, a subclass of DCs. In addition, the D2SC/wt cells secrete a large amount of type I IFN-α and IFN-β when interacting with viruses, bacterial as well as CpG-DNA. The D2SC/wt cells also expressed extremely high copy numbers of type I interferon mRNA as detected by in situ hybridization study (Scand. J. Immunol. 1997, 46:235-41; Eloranta M L., et al unpublished data). Therefore, it was concluded that the D2SC/wt cells is the putative human natural interferon producing cells in mouse and is a pDC/IPCs subclass of dendritic cells.

Plasmid DNA Vector

A resent study has shown that the empty plasmid pcDNA3 contains a number of unmethylated CpG motifs in the backbone of the vector (Science 1996, 273:352-354). High levels of IFN-α and IL-6 production were induced in porcine leukocytes by incubating the cells with plasmid pcDNA3. Methylation of all cytidines in CpG dinucleotides of pcDNA3 abolished the IFN-αinducing capacity (Vet Immunol Immunopathol. 200, 78:45-56).

pVAX-1© was constructed by modifying the pcDNA3.1 vector according to the recommendation by the FDA (Invitrogen, CA, USA). pVAX-1© is a 3.0 kb plasmid vector designed for use in the development of cancer vaccines in humans.

A Minigene Encodes the Fusion Peptide of e1a2 is Cloned into Plasmid Vector Containing CpG-Motifs PCR primers were designed to amplify the nucleotide sequences that encode for predicted MHC class I-binding e1a2 fusion peptide. Production of the minigene started with a fill-in reaction (Pharmacia) using the following overlapping primers: 5'-TGCTAGCATGATCTGGCC-CAACGACGGCGAGGGCGCCTTCCACGGCGAC-GCCGAGGCCCTGCAGCGC-3' (see SEQ ID NO: 1) and 5'-AATCGATCACAGGCCCTGGGGCTCGAAGT-CGCTGGCCACGGGGCGCTGCAGGGC-3' (see SEQ ID NO: 2). The reaction mixture included, in addition to the two primers above, also the Klenow fragment (E. coli DNA polymerase I), dNTPs and enzyme buffer, according to the manufacture's recommendation. The reaction was carried out at room temperature for 1 h followed by PCR reaction using the same primers and by adding PCR buffer, Taq DNA polymerase, dNTPs and run for 95° C. 1 min, followed by 35 cycles of 95° C. 30 s, 65° C. 30 s and 72° C. 30 s. The obtained PCR fragment was isolated and initially cloned into a pUC19 plasmid vector (New England BioLabs) at the Nhe I/Cla I site. The Nhe I/Cla I fragment was then inserted into pBK-CMV vector (Stratagene). A Nhe I/Kpn I fragment comprising the e1a2 fusion minigene in the pBK-CMV was finally cloned into Nhe1 and Kpn1 site of the pVAX-1 vector (Invitrogen, CA, USA). Once incorporated into the vector, the e1a2 mini-fusion gene is under control of the CMV promoter. The pVAX-e1a2 construct was confirmed by DNA digestion and DNA sequencing. The plasmid was amplified using Qiagen EndoFree Plasmid Maga kit according to the manufacture's instruction (Qiagen, Santas Clarita, Calif., USA). Purity of plasmid DNA was determined by UV spectrophotometry and agarose gel electrophoresis. Purified DNA with an OD 260 nm/OD 280 nm absorbance ratio of greater than 1.9 was used.

Drawings of the empty pVAX-1 vector and vector containing nucleotide sequence encoding the mini-e1a2 fusion protein, pVAX-e1a2 are found in FIG. 10. The mini-e1a2 fusion gene sequences and corresponding polypeptide sequence are shown in SEQ ID NO: 3 and SEQ ID NO: 4, respectively.

The pVAX-e1a2 plasmid construct was tested for the production of correctly sized product by an in vitro transcription-coupled translation assay (TNT, Promega). Approximately 1 µg of plasmid DNA was incubated for 2 h at 30° C. in a 50 µl volume containing a mixture of 25 µl rabbit reticulocyte lysate, 2 µl of TNT reaction buffer, 1 µl of TNT T7 RNA polymerase, 1 µl of a 1 mM amino acid mixture minus methionine, 4 µl of (35S) methionine at 10 mCi/mi and 1 µl RNA RNAasin ribonuclease inhibitor at 40 U/µ1. A 30 volume of the reaction was loaded onto a 16% SDS polyacrylamide gel. After drying, the gel was exposed to autoradiography film. The results are illustrated in FIG. 10, indicating presence of the e1a2 fusion protein in pVAX-e1a2 but not in empty pVAX-1. In addition, the transcript of pVAX-e1a2 was detected in COS-7 cell line after transfection in the presence of Lipofectin (data not shown). Taken together, the pVAX-e1a2 plasmid DNA, containing the 96 bp nucleotide sequences spanning the fusion region of e1a2 gene, is transcribed and expressed by transfected cells.

Naive T Cell Activation

Single cell suspensions from spleens were prepared. T cells were isolated from spleens of BALB/c mice and C57BL/6J mice. Percoll gradient-enriched T cells from spleens of C57BL/6J mice were used as a source of allogenic T cells. CD4+ or CD8+ T cells from BALB/c mice were purified using the MACS CD4 or CD8 microBeads according to the manufacture instruction (Miltenyi Biotec, Germany). Stimulators (DCs) were irradiated (50 Gy, from $^{137}$Cs) and added in graded doses to responder cells (spleen cells or T cells, 2×10$^5$ cells/well) in 96-well round-bottom microtiter plates (Becton, Dickinson). Experiments were performed in triplicates in a final volume of 200 μl/well. Proliferation was measured by the uptake of [$^3$H]-thymidine (1 μCi/well) (Amersham International, Amersham, UK) added for 6 h on day 3 prior to harvesting onto glass fiber filter and subjected to scintillation counting (Beta counter, Pharmacia).

Gene-Modification Elevates the Capacity of Immature DCs to Stimulate T Cells

As a type of immature DC, the non-modified D2SC/wt cells are poor T cell stimulator. Thus, the capacity of D2SC/wt and D2SC/CD40L to induce a naive allogeneic T cell proliferation was compared. The allogeneic T cell proliferation is 8-fold higher when stimulated by CD40L gene-modified DCs (D2SC/CD40L) in comparison to non-modified parental DCs (D2SC/wt) as illustrated in FIG. 11A.

The capacity of D2SC/wt and D2SC/CD40L to induce a naive autologous T cell proliferation was compared. The autologous T cell proliferation is 4-fold higher when stimulated by gene-modified DCs compare to non-modified parental DCs, illustrated in FIG. 11B. DCs engineered to secrete GM-CSF (D2SC/GM-CSF) have also induced a more potent allogenic and autologous T cell proliferation (data not shown). Thus, expression of CD40 ligand on DCs is functionally active and involved in stimulation of T cells. Noteworthy, the D2SC/CD40L cells may have acquired the capacity to direct priming autologous T cells in vivo after injection. It was also found that DCs migrate into spleen and lymph node after subcutaneous injection (data not shown).

Tumor Antigen Preparation

Autologous tumor lysate was prepared from BM185/wt cells. Tumor cells were subjected to several cycles of freezing (liquid nitrogen) and thawing (37° C. water bath). The tumor cell lysate was further sonicated at 4° C. for 30 min. Cell debris was removed by centrifugation at 2 500 rpm for 10 min at 4° C. Soluble proteins were collected and the protein concentration was determined by the Bradford method (Protein Assay, Bio-Rad, CA, U.S.A).

Pulsing DCs with Tumor Antigens or Tumor Antigenic Peptide

DCs were pre-incubated with tumor lysate (100 μg/10$^6$ cells), overnight at 37° C. in 7% CO$_2$. DCs were detaches from culture flask with PBS/5 mM EDTA solution and washed carefully before injected into mice. In peptide pulsing experiment, 10$^6$ cells were pulsed 2 h with 10 μM of peptides at 37° C. in FCS free medium in 5% of CO$_2$.

Immunization with Vaccine Composition

Female BALB/c (H-2d) mice 6-8 weeks of age were purchased from M&B (Denmark) and maintained under standard conditions at the Animal Facility at Uppsala University. All animal experiments were conducted in accordance with the Animal Care Committee (ref. nr. C63/97, C36/1).

For the tumorgenicity study, increasing doses of viable BM185/wt cells were given subcutaneous (s.c.) to immunocompetent syngeneic mice. Injection of 500 cells into 6-8 weeks old mice caused 100% mortality within a 3-4 week period (see top of FIG. 14). A lethal dose of injection (800 tumor cells/mouse) as generally used in the present study.

The minimal dose of gene-modified DCs required for the effective elimination of tumor outgrowth was sought. DCs were loaded with tumor lysate overnight prior to immunization. A single vaccination with 10$^6$ D2SC/CD40L cells was found to be sufficient as therapeutic treatment in tumor-established mice, see FIG. 12A.

Tumor-bearing mice were treated once (either at tumor site or at a distinct site) with tumor-lysate pulsed D2SC/CD40L (p<0.001) or D2SC/GM-CSF cells (p<0.001). Immunization with CD40L or GM-CSF gene-modified DCs induces effective anti-tumor immune response. A single vaccination was sufficient to eradicate pre-existing tumor cells and all treated mice were tumor free (100%), as is shown in FIG. 12B. Result represents one of four repeated experiments.

The induced anti-tumor immune response is associated with the in vivo generation of tumor-specific cytotoxic T cells (CTLs). In vitro expanded CTLs specifically kill parental tumor cells, BM185 cells (FIG. 13A), but not the syngeneic tumor cell line, A20 (FIG. 13B).

These studies have shown that the genetically engineered DCs, D2SC/CD40L cells have the capacity to stimulate a potent therapeutic immune response in tumor-bearing mice.

An example of a tumor-bearing mouse model for therapeutic and protective vaccinations employed by the present invention is illustrated in FIG. 14.

Pre-Incubation of Plasmid DNA and DCs

In order to enhance the binding of plasmid to DCs and permit the endocytosis of plasmid DNA into DCs, a co-centrifugation method was developed. In brief, gene-modified DCs, grown in optimal density in cell culture flask, were detached with PBS/5 mM EDTA solution at 37° C. for 20 min. DCs were collected and washed in PBS (free of Ca+, Mg+) and were suspended in PBS. Plasmid DNA (1 mg/ml) was added to 10$^7$ DCs/ml and they were co-centrifuged at 10 000 rpm, at room temperature for 30 min. After centrifugation, plasmid DNA/DCs mixture was incubated for additional 3 hours at 37° C., 7% CO$_2$ prior to injection into mice.

CTL Assay

In order to investigate the development of cytocoxic T cells (CTLs) in vivo after the vaccination treatment, spleens and lymph nodes (LN) from either normal or vaccinated mice were isolated. T cells were purified by either Percoll gradient method or magnetic cell sorting using MACS CD4 or CD8 MicroBeads according to manufacture instruction (Miltenyi Biotec, Germany). T cells were re-stimulated for 5-7 days with BM185/wt (200 Gy, $^{137}$Cs γ-radiation) or BM185/CD40L (200 Gy) in the presence of rhIL-2 (10 ng/ml). Dead cells were removed and viable cells are used as effectors in a standard 4 h $^{51}$Cr release cytotoxicity assay. In brief, target cells were pre-labeled with $^{51}$Cr (25 μCi/10$^6$ cells) at 37° C. for 2 h. The viable effector cells were incubated for 4 hours with pre-labeled target cells at various effector-to-target ratios. Cytolysis was measured by the release of $^{51}$Cr into the medium and the results represent triplicate samples. The percentage of specific lysis was calculated according to the following formula:

$$\text{percentage specific lysis} = 100 \times \frac{\text{experimental lysis} - \text{spontaneous lysis}}{\text{maximum lysis} - \text{spontaneous lysis}}$$

Con A Activated T Cell Blasts

In a control experiment, spleen cells from normal mice were incubated for 48 h at 2×10$^6$ cells/ml in RPMI1640 medium supplied with penicillin/streptomycin, 10% FCS, 10 mM Hepes, $3 \times 10^{-5}$ M 2-mercaptoethanol and 3 µg/ml Con A (Sigma). Con A activated T cell blasts were used as effector cells against tumor cells (negative control).

Statistical Analysis

All animal experiments were conducted with a minimum of five or ten animals per group. All studies were repeated at least three times with similar results. Survival differences were analyzed with the Chi-square test to interpret the significance of differences between experimental groups.

Investigation of DNA and DCs Vaccine Efficiency

A lethal dose of viable parental BM185/wt tumor cells were injected subcutaneous (s.c.) into the right flank of each mouse (5 mice/group) on day 0. On day 7, 14 and 21 mice were immunized at the tumor site with (1) PBS; (2) empty pVAX-1 vector (100 µg/mouse); (3) pVAX-e1a2 (100 µg/mouse); (4) D2SC/CD40L alone without loading of antigen; (5) D2SC/CD40L cells pre-incubated with pVAX-e1a2 plasmid DNA ($10^6$ cells/100 µg plasmid DNA/mouse). The tumor size was monitored twice per week. When the tumor is detectable, mice were considered to be at the end point of survival and were sacrificed.

Despite the presence of possible immune stimulating CpG-motifs in plasmid vector back bone, treatments of tumor-bearing mice with either empty pVAX-1 vector or pVAX-e1a2 alone failed to eliminate the pre-existing tumor. In the absence of tumor antigen, treatment of tumor-bearing mice with D2SC/CD40L cells failed to eliminate tumors in mice. In contrast, a superior anti-tumor effect is demonstrated by co-delivery of pVAX-e1a2 with D2SC/CD40L cells. The vaccination with pVAX-e1a2 and D2SC/CD40L cells resulted in eliminating of pre-existing tumor cells in all treated mice, 100% efficient (p<0.01). The capacity of induced anti-tumor immune response to protect mice from rechallenge of parental tumor cells was further investigated. One week after the last vaccination, the tumor free mice were given at a distinct site with a lethal dose of parental tumor cells. FIG. 15 shows that tumor-bearing mice treated repeatedly with pVAXe1a2 and DC/CD40L develop efficient anti-tumor immunity sufficient to protect mice against rechallenge of tumor cells and approximately 80% mice were protected and remained tumor free (result presents one of three repeated experiments).

Immunization with the vaccine of present invention, pVAX-e1a2 and DC/CD40L generates tumor-specific T-cells in vivo that can kill tumor cells. The T cells from tumor free mice were analyzed. In vitro cultured CTLs specifically kill parental BM185 tumor cells. These tumor-specific CTLs recognize e1a2 peptide, but not the low affinity MHC class I-binding peptide 8, loaded onto RAM-s cells (FIG. 16)

Comparison of Different Vaccination Compositions

The efficacy of vaccine composition of the present invention was compared with other vaccination strategies capable of treating mice with pre-existing bcr/abl positive tumors and protecting mice against re-challenge of parental tumor cells.

Mice (5 mice/group) were inoculated subcutaneous at right flank with a lethal dose of live BM185 wt tumor cells on day 0. On day 7, 14 and 21, mice were immunized at the tumor site with (a) PBS; (b) pVAX-e1a2 (100 µg/mice); (c) e1a2 peptide (AFHGDAEAL, 10 µM/mice, SEQ ID NO: 5); (d) D2SC/wt cells pulsed with e1a2 peptide ($10^6$ cells/10 µM/mice); (e) D2SC/CD40L cells pulsed with e1a2 peptide ($10^6$ cells/10 µM peptide/mouse,); (I) D2SC/CD40L cells pulsed with loe MHC-binding peptide (HGDAEALQR, $10^6$ cells/10 µM/mice); (g) D2SC/CD40L cells pulsed with tumor lysate derived from BM185 cells; (h) D2SC/CD40L cells pre-incubated with pVAX-e1a2 plasmid DNA ($10^6$ cells/100 µg/mouse). For the immune protection study, one week after the last vaccination, tumor free mice were rechallenged with a lethal dose of live parental BM185 wt tumor cells at left flank. The tumor size was monitored twice per week. When the tumor is detectable, mice were considered to be at the end point of survival and were sacrificed. Experiments were repeated three times and results represent one of these experiments.

The vaccine composition (D2SC/CD40L pre-incubated with pVAX-e1a2, filled circle dots) of the present invention is most effective therapeutic strategy (p<0.01) to eliminate pre-existed tumor and all treated mice were tumor free (100%). The efficacy and capacity of the immune response evoked by vaccination to protect host against tumor challenge was investigated. Tumor free mice are injected with a lethal dos of parental live tumor cells at a distant site of vaccination, and 80% of these mice are protected and remained tumor-free for several months after tumor challenge (p<0.01), see FIG. 17.

In line with the previous study, vaccination with either pVAX-e1a2, or e1a2 peptide or D2SC/CD40L cells pulsed with peptide, which has low affinity for MHC-I, failed to eradicate pre-existing tumor in mice.

Pulsing MHC class-I binding peptide onto D2SC/CD40L cells apparently enhanced tumor antigen presentation. Treatment of tumor-bearing mice with D2SC/CD40L loaded with e1a2 peptide induces anti-tumor immunity. However, this strategy is 2-fold less efficient as compare to the treatment using vaccine of the present invention.

The superior efficacy of the present vaccine composition of pVAX-e1a2 and DC/CD40L, may underline one of the key elements in the present vaccine composition. In addition to antigen, the pVAX-e1a2 plasmid DNA contains CpG motifs. CpG-motifs are known to stimulate and activate DCs via TLR9 pathway resulting production of type I interferon. It was found that D2SC/wt and D2SC/CD40L cells have TLR9. Earlier studies have shown that D2SC/wt cells secreted type I IFN-α and IFN-β after stimulating by virus and bacteria.

Thus, in comparison to the treatment of tumor-bearing mice with injection of DC/CD40L pulsed tumor antigen-peptide, the possibility of type I IFN production in vivo and stimulating immune response by CpG-motifs in plasmid back bone may contribute to the superior efficiency of the present vaccine composition (FIG. 17).

Tumor-Specific and Tumor Antigen-Peptide Specific CTLs are Generated after Variety Vaccination Strategies Immunization with the vaccine of present invention generates tumor-specific and e1a2-peptide specific T-cells in vivo that can kill tumor cells. For in vitro stimulation of T cells, DCs or tumor cells were first pulsed with e1a2 peptide and then irradiated and used as stimulators. T cells from tumor-free mice after the tumor challenge were co-stimulated with these DCs or tumor cells for seven to ten days. Cell culture supernatant was collected and stored at −80° C. for analysis of cytokine secretion. Viable cells (>80% CD8+ T cells) were used as effector cells for CTL assay.

CTLs generated in vitro were tested for their capacity to lyse tumor cells. Tumor-bearing mice were treated with (a) PBS; (b) e1a2 peptide; (c) pVAX-e1a2; (d) D2SC/CD40L cells pulsed with e1a2 peptide; (e) D2SC/CD40L cells pulsed with tumor-lysate; (f) D2SC/CD40L cells pre-incubated with pVAX-e1a2 plasmid DNA. T cells were isolated from mice after the challenge with parental tumor cells. The anti-tumor immunity was provoked in tumor-free mice treated with either DC/CD40L loaded with tumor antigens (lysate or e1a2 peptide) or DC/CD40L pre-incubated with pVAX-e1a2 (FIG. 18A). In addition, the secretion of IFN-γ was detected in supernatant of CTLs culture (on day 6), see Table II.

TABLE II

| Vaccine composition | IFN-γ (ng/ml) |
|---|---|
| Normal (control) | 1.5 |
| PBS | 2.9 |
| e1a2-peptide | 6.1 |
| pVAX-e1a2 | 4.5 |
| D2SC/CD40L/e1a2-peptide | 15.2 |
| D2SC/CD40L/lysate | 23 |
| D2SC/CD40L/pVAX-e1a2 | 21.5 |

Treatment of mice with neither tumor-peptide nor tumor-peptide containing plasmid induces tumor-specific CTLs. In contrast, repeated vaccinations with pVAX-e1a2 plasmid DNA vector and DC/CD40Ls induced a strong tumor-specific CTL response paralleled by a therapeutic response.

Tumor-Specific CTLs Recognize Tumor-Peptide Presented by the Vaccine Composition of the Present Invention.

The capacity of tumor-specific CTLs to kill the peptide pulsing target cells was investigated. The TAP deficient RMA-S cells were loaded with e1a2 peptides. The RMA-S cells lack the ability of loading their own MHC class-I. Thus, for RAM-S cells pulsed with e1a2 peptide, the e1a2 peptide was the only peptide present. Presenting of e1a2 peptide on RAM-S cells is recognized by CTLs generated in tumor-free mice after vaccinations with DC/CD40L loaded with tumor-antigens (tumor lysate or e1a2 peptide) and DC/CD40L incubated with pVAX-e1a2 (FIG. 18B). The peptide specific CTLs do not kill parental RMA-S cells (without loading of peptide, data not shown). It was concluded that the in vivo-generated anti-tumor immunity by the vaccinations is tumor-antigen specific and directed against parental BM185 cells.

Frequency of e1a2-Peptide Specific CTLs Generated after Vaccinations

Expansion of the e1a2-peptide specific CTLs were obtained by co-stimulation of purified T cells (containing of CD8+ cells, 90% and CD4+, 10%) with D2SC/CD40L cells pulsed with e1a2-peptide (50Gy) in the presence of rhIL-2 (25 ng/ml, R&D, UK). After seven days of stimulation, approximately 85% T cells obtain are CD8+ T cells (FIG. 19).

The frequency of tumor peptide, e1a2-peptide, specific CD8+ T cells in vitro was studied using a DimerX Peptide presentation method (BD Bioscience, U.S.A). In brief, H-2L$^d$:Ig is mixed with peptide (e1a2 peptide or peptide 8) at 160 molar excess at 37° C. overnight. CD8+ T cells are suspended in a concentration of $10^6$ cells per 50 μl. 2 μg of peptide-loaded H-2L$^d$:Ig complex protein is added to the T cells and incubated 60 min at 4° C. A PE-conjugated rat anti-mouse IgG1 antibody is used to detect complex protein binding using flow cytometer.

The e1a2-peptide specific CD8+ T cells that recognize tumor cells and e1a2-peptide pulsed target cells are shown to bind to the e1a2-peptide loaded H-2L$^d$:Ig complex (FIG. 20). In consist with the CTL assay analysis, treatment of mice with DC/CD40L and pVAX-e1a2, generates 8-fold more e1a2-peptide specific CTLs than treatment with pVAX-e1a2 alone and approximately 2-fold more e1a2-peptide specific CTLs in comparison to the treatment with DC/CD40L loaded e1a2.

In summary, a novel vaccination composition and strategy to enhance the anti-tumor immunity against pre-existing bcr/abl tumor is presented. In this strategy, a genetically modified subclass of DCs, pDCs/IPCs, and a CpG containing plasmid vector that comprises the gene encoding e1a2 tumor-specific peptide were used. Treatments of tumor-bearing mice with repeated vaccinations of the DC/CD40L and the CpG-motif-containing pVAX-e1a2 elicited a tumor-specific and e1a2-peptide specific T cell response. It was further demonstrated that the e1a2-peptide specific CTLs induced in vivo recognize e1a2 peptide both in CTL assay and identified by indirect immunofluorescent staining of e1a2-peptide on these T cell surface. Apparently vaccination induces e1a2-specific T cells that recognize tumor cells and kill them in situ. The new generated e1a2-specific T cells may play an important roll in protecting the host against rechallenge of parental tumor. The vaccine compositions of the invention are effective in eliminating pre-existing bcr/abl positive tumor and protecting animal from challenge of viable parental tumor. Thus, the present vaccine composition is well adapted as therapeutic and pharmaceutical composition for Philadelphia chromosome-positive tumor.

Proposed Mechanism for Vaccine Composition

Based on the experiment results presented in the present invention and the study by others in the field of tumor immunology, a hypothesis of the possible mechanisms and key factors that contribute to the success of the present invention is presented herebelow and in connection with FIG. 21.

After enforcement, the plasmid DNA encoding tumor-peptide (CpG-DNA-e2a2) is bound to DCs. Most of the CpG-DNA-e2a2 plasmid DNA is possibly endocytosed and followed by presentation on MHC molecules. The CpG-motifs in the plasmid DNA subsequently bind to TLR9 and active the toll-like receptor pathway in DCs.

Activation of TLR9 pathway may lead to secretion of type I IFN-α and IFN-β. This event may occur during the incubation of the CpG-DNA-e2a2 and DCs. Thus, before, during and/or after the pre-incubation it is preferred to enhance the binding of plasmid DNA to DCs, e.g. by co-centrifugation.

The DCs cells are genetically modified to express CD40L. Thus the DCs express B7 and CD40L, two of the most important T cell activation signals. In the presence of CD40L, B7 and type I interferon, the gene-modified DCs present the tumor peptide to immune cells, such as naive T cells and active naive DCs via CD40-CD40L interaction. In vivo, DCs may take up and present non-bound antigens/or CpG-DNA-e2a2. Both types of dendritic cells, pDCs/IPCs/CD40L/B, and activated DCs carrying tumor antigen migrate to lymphoid tissue and activated immune cells including naive T cells, B cells and DCs. Cross-priming and direct priming of the host immune system may take place at the same time and may be present in same tissues. Production of cytokines, such as IL12, IL15, IFN-γ, type I TNF-α and other Th1 cytokine may take place. The CD40L modified pDCs, expressing B7 molecules, can present tumor peptide direct to naive CD8+ T cells and activate the tumor-specific CTLs, thereby obtaining a faster, increased and more efficient therapeutic and protective immune response. The final outcome of vaccination with the present invention is the generation of e1a2-specific CTLs and eliminating the pre-existing tumor. The in vivo induced anti-tumor immunity protects the host against tumor challenge.

Thus, our novel vaccine strategy underlines the unique combination of activating innate immunity and adaptive immunity. This novel vaccine composition is suitable for designing pharmaceutical vaccine composition directed for either treating or preventing diseases in humans and animals.

It will be understood by a person skilled in the art that various modifications and changes may be made to the present invention without departure from the scope thereof, which is defined by the appended claims.

What is claimed is:

1. A method of treating a Philadelphia chromosome-positive tumor in a subject, the method comprising administering to the subject a therapeutic composition comprising an incubated combined mixture of:
   (a) a first component comprising (i) Philadelphia chromosome-positive tumor lysate, (ii) plasmid encoding bcr/abl fusion protein, or (iii) bcr/abl fusion peptide; and
   (b) a second component comprising plasmacytoid dendritic cells expressing Toll-like receptor 9 and modified for stable expression of CD40 ligand or GM-CSF by a nucleotide sequence engineered into said plasmacytoid dendritic cells.

2. The method according to claim 1, wherein the second component comprises plasmacytoid dendritic cells expressing Toll-like receptor 9 and modified for stable expression of CD40 ligand.

3. The method according to claim 1, wherein the second component comprises plasmacytoid dendritic cells expressing Toll-like receptor 9 and modified for stable expression of GM-CSF.

4. The method according to claim 2, wherein the first component comprises Philadelphia chromosome-positive tumor lysate.

5. The method according to claim 2, wherein the first component comprises plasma encoding bcr/abl fusion protein.

6. The method according to claim 2, wherein the first component comprises bcr/abl fusion peptide.

7. The method according to claim 3, wherein the first component comprises Philadelphia chromosome-positive tumor lysate.

8. The method according to claim 3, wherein the first component comprises plasma encoding bcr/abl fusion protein.

9. The method according to claim 3, wherein the first component comprises bcr/abl fusion peptide.

* * * * *

UNITED STATES PATENT AND TRADEMARK OFFICE
CERTIFICATE OF CORRECTION

| | |
|---|---|
| PATENT NO. | : 11,298,398 B2 |
| APPLICATION NO. | : 16/985393 |
| DATED | : April 12, 2022 |
| INVENTOR(S) | : Mallen Huang |

It is certified that error appears in the above-identified patent and that said Letters Patent is hereby corrected as shown below:

On the Title Page

Item (63), change "Continuation" to --Divisional--.

Signed and Sealed this
Twelfth Day of July, 2022

Katherine Kelly Vidal
*Director of the United States Patent and Trademark Office*

SEQUENCE LISTING

<160> NUMBER OF SEQ ID NOS: 14

<210> SEQ ID NO 1
<211> LENGTH: 67
<212> TYPE: DNA
<213> ORGANISM: Artificial Sequence
<220> FEATURE:
<223> OTHER INFORMATION: Synthetic primer

<400> SEQUENCE: 1
tgctagcatg atctggccca acgacggcga gggcgccttc cacggcgacg ccgaggccct     60
gcagcgc                                                               67

<210> SEQ ID NO 2
<211> LENGTH: 54
<212> TYPE: DNA
<213> ORGANISM: Artificial Sequence
<220> FEATURE:
<223> OTHER INFORMATION: Synthetic primer

<400> SEQUENCE: 2
aatcgatcac aggccctggg gctcgaagtc gctggccacg gggcgctgca gggc           54

<210> SEQ ID NO 3
<211> LENGTH: 96
<212> TYPE: DNA
<213> ORGANISM: Homo sapiens
<220> FEATURE:
<221> NAME/KEY: CDS
<222> LOCATION: (1)..(96)

<400> SEQUENCE: 3 atg atc tgg ccc aac gac ggc gag ggc gcc ttc cac ggc gac gcc gag       48
Met Ile Trp Pro Asn Asp Gly Glu Gly Ala Phe His Gly Asp Ala Glu
1               5                   10                  15 gcc ctg cag cgc ccc gtg gcc agc gac ttc gag ccc cag ggc ctg tga      96
Ala Leu Gln Arg Pro Val Ala Ser Asp Phe Glu Pro Gln Gly Leu
            20                  25                  30

<210> SEQ ID NO 4
<211> LENGTH: 31
<212> TYPE: PRT
<213> ORGANISM: Homo sapiens

<400> SEQUENCE: 4

Met Ile Trp Pro Asn Asp Gly Glu Gly Ala Phe His Gly Asp Ala Glu
1               5                   10                  15

Ala Leu Gln Arg Pro Val Ala Ser Asp Phe Glu Pro Gln Gly Leu
            20                  25                  30

<210> SEQ ID NO 5
<211> LENGTH: 9
<212> TYPE: PRT
<213> ORGANISM: Homo sapiens

<400> SEQUENCE: 5

Ala Phe His Gly Asp Ala Glu Ala Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide with low binding to mouse
      MHC-I antigen (H-2Kd)

<400> SEQUENCE: 6

His Gly Asp Ala Glu Ala Leu Gln Arg
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide that does not bind to mouse
      MHC-I antigen (H-2Kd)

<400> SEQUENCE: 7

Ala Thr Gly Phe Lys Gln Ser Ser Lys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 8

Asp Ala Glu Ala Leu Gln Arg Pro Val
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 9

Glu Ala Leu Gln Arg Pro Val Ala Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 10

Gly Ala Phe His Gly Asp Ala Glu Ala
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 11

Ala Glu Ala Leu Gln Arg Pro Val Ala
1               5

```
<210> SEQ ID NO 12
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 12

Glu Gly Ala Phe His Gly Asp Ala Glu
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 13

Phe His Gly Asp Ala Glu Ala Leu Gln
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 14

Gly Asp Ala Glu Ala Leu Gln Arg Pro
1               5
```